(12) United States Patent
Massade et al.

(10) Patent No.: US 11,939,577 B2
(45) Date of Patent: Mar. 26, 2024

(54) ANTISENSE RNA TARGETING PMP22 FOR THE TREATMENT OF CHARCOT-MARIE-TOOTH 1A DISEASE

(71) Applicants: CENTRE NATIONAL DE LA RECHERCHE SCIENTIFIQUE, Paris (FR); INSTITUT NATIONAL DE LA SANTE ET DE LA RECHERCHE MEDICALE (INSERM), Paris (FR)

(72) Inventors: Liliane Massade, Cachan (FR); Charbel Massaad, Arcueil (FR); Susan Boutary, Arcueil (FR); Giorgia Maria Laura Urbinati, Paris (FR); Patrick Couvreur, Paris (FR); Didier Desmaële, Fresnes (FR)

(73) Assignees: CENTRE NATIONAL DE LA RECHERCHE SCIENTIFIQUE, Paris (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 242 days.

(21) Appl. No.: 17/279,206

(22) PCT Filed: Sep. 24, 2019

(86) PCT No.: PCT/EP2019/075736
§ 371 (c)(1),
(2) Date: Mar. 24, 2021

(87) PCT Pub. No.: WO2020/064749
PCT Pub. Date: Apr. 2, 2020

(65) Prior Publication Data
US 2022/0002721 A1    Jan. 6, 2022

(30) Foreign Application Priority Data
Sep. 25, 2018  (EP) ..................................... 18306241

(51) Int. Cl.
| | | |
|---|---|---|
| *C12N 15/113* | (2010.01) | |
| *A61K 9/51* | (2006.01) | |
| *A61K 45/06* | (2006.01) | |
| *A61K 47/69* | (2017.01) | |

(52) U.S. Cl.
CPC .......... *C12N 15/113* (2013.01); *A61K 9/5123* (2013.01); *A61K 45/06* (2013.01); *A61K 47/6929* (2017.08); *C12N 2310/11* (2013.01); *C12N 2310/14* (2013.01); *C12N 2310/351* (2013.01); *C12N 2320/32* (2013.01)

(58) Field of Classification Search
CPC .............. C12N 15/113; C12N 2310/11; C12N 2310/14; C12N 2310/351; A61K 9/0019; A61K 31/713; A61K 47/6929

USPC .................... 435/6.1, 91.1, 91.31, 455, 458; 514/44 A; 536/23.1, 24.5
See application file for complete search history.

(56) References Cited

U.S. PATENT DOCUMENTS

| | | | |
|---|---|---|---|
| 2015/0353917 A1* | 12/2015 | Miller ................... | C12N 15/102 435/441 |
| 2018/0066257 A1 | 3/2018 | Choi et al. | |
| 2022/0251553 A1* | 8/2022 | Hung ................... | A61K 9/0019 |

FOREIGN PATENT DOCUMENTS

| | | | | |
|---|---|---|---|---|
| CA | 3043148 A1 | * | 5/2018 | ............. A61K 35/30 |
| WO | 2005123128 A2 | | 12/2005 | |
| WO | 2005123128 A3 | | 12/2005 | |
| WO | 2011/005786 A2 | | 1/2011 | |
| WO | 2012139081 A2 | | 10/2012 | |
| WO | 2012139081 A3 | | 10/2012 | |
| WO | 2016/011083 A2 | | 1/2016 | |
| WO | 2016011080 A2 | | 1/2016 | |
| WO | 2017/156242 A1 | | 9/2017 | |
| WO | WO-2017156242 A1 | * | 9/2017 | ......... A61K 31/7088 |

OTHER PUBLICATIONS

Joshi, B. H. & Pachchigar, K. P., "siRNA: novel therapeutics from functional genomics", Biotechnology and Genetic Engineering Reviews vol. 30 No. 1, 2014.
Hien Tran Zhao et al: "PMP22 antisense oligonucleotides reverse Charcot-Marie-Tooth disease type 1A features in rodent models", Journal of Clinical Investigation, vol. 128, No. 1, pp. 359-368, Jan. 2, 2018.
Hien Tran Zhao et al: "PMP22 antisense oligonucleotides reverse Charcot-Marie-Tooth disease type 1A features in rodent models", Supplemental Materials, Journal of Clinical Investigation, vol. 128, No. 1, pp. 359-368, Jan. 2, 2018.
Juneja et al: "Challenges in modelling the Charcot-Marie-Tooth neuropathies for therapy development", Journal of Neurology Neurosurgery & Psychiatry, Jul. 17, 2018.
Lee et al: "Pmp22mutant allele-specific siRNA alleviates demyelinating neuropathic phenotypein vivo", Neurobiology of Disease, vol. 100, pp. 99-107, Jan. 17, 2017.
Masaad-Massade et al: "New Formulation for the Delivery of Oligonucleotides Using "Clickable" siRNA-Polyisoprenoid-Conjugated Nanoparticles: Application to Cancers Harboring Fusion Oncogenes", Bioconjugate Chemistry, vol. 29, pp. 1961-1972, 2018.

(Continued)

*Primary Examiner* — Jane J Zara
(74) *Attorney, Agent, or Firm* — WCF IP

(57) ABSTRACT

The present invention relates to antisense RNAs targeting PMP22 and able to inhibit from 40% to 60% the expression of PMP22 in the cells and a pharmaceutical composition comprising thereof. The antisense RNAs are preferably siRNA and are preferably provided in the form of nanoparticles. The present invention also relates to the use of these antisense RNAs targeting PMP22 for the treatment of Charcot-Marie-Tooth 1A disease.

13 Claims, 21 Drawing Sheets
Specification includes a Sequence Listing.

(56) References Cited

OTHER PUBLICATIONS

Ridler: "Peripheral neuropathies: Antisense therapy for Charcot-Marie-Tooth disease?", Nature Reviews, vol. 14, No. 2, pp. 64-64, Dec. 22, 2017.
Shy: "Antisense oligonucleotides offer hope to patients with Charcot-Marie-Tooth disease type 1A", Jornal of Clinical Investigation, vol. 128, No. 1, pp. 110-112, Jan. 2, 2018.

* cited by examiner

ANTISENSE RNA TARGETING PMP22 FOR THE TREATMENT OF CHARCOT-MARIE-TOOTH 1A DISEASE

FILED OF THE INVENTION

The present invention relates to the treatment of Charcot-Marie-Tooth 1A (CMT-1A) disease.

BACKGROUND

CMT-1A neuropathy is due to altered peripheral nerve myelin, resulting in demyelination and causing a severe and invalidating disease. Myelin sheaths surrounding peripheral nerve axons are formed by Schwann cells. They are essential for the rapid and accurate transmission of electrical impulses via saltatory conduction. The predominant subtype of Charcot-Marie-Tooth diseases is CMT-1A, accounting for more than 50% of all patients. It is associated with an interstitial chromosomal duplication of 17p11.2, resulting in the overexpression of the gene encoding the peripheral myelin protein of 22 kDa (PMP22), responsible for the disease, characterized by the loss of muscle and sensory functions.

Several attempts were made to cure CMT-1A disease or at least to ameliorate its invalidating symptoms.

One of the promising molecules was ascorbic acid. In animal models of CMT-1A overexpressing PMP22, ascorbic acid treatment resulted in substantial amelioration of the disease phenotype and reduced the expression of PMP22. Unfortunately, a clinical trial testing the effects of ascorbic acid supplementation in CMT-1A patients had no beneficial effects when compared with placebo. Thus, there is so far no clinical evidence to support ascorbic acid treatment in adults with CMT-1A.

Anti-progesterone therapy was found to significantly increase muscle strength and prevent axon loss in PMP22 transgenic rats, although myelin sheath thickness was not affected. Unfortunately, currently available progesterone antagonists are too toxic to be safely administered to patients.

Neurotrophin-3 (NT3), a neurotrophic factor known to promote axonal growth, was tested with favorable results in two animal models, and in a pilot study involving eight CMT-1A patients.

However, there is currently no effective drug for CMT-1A and supportive treatments are limited to physical therapy, orthotics, surgical treatment of skeletal and soft tissue abnormalities, as well as symptomatic drug treatment.

There is therefore a need to provide solutions for the treatment of CMT-1A disease.

DESCRIPTION OF THE INVENTION

The Inventors have found that antisense RNAs targeting PMP22, in particular using a RNA interference (RNAi), are highly efficient for the treatment of Charcot-Marie-Tooth 1A. The Inventors have indeed shown that administering a small interfering RNA (siRNA) targeting PMP22 via the intravenous route enabled restoration of locomotion and strength identical to wild type mice in a murine model of Charcot-Marie-Tooth 1A disease, wherein PMP22 is 1.5-fold overexpressed in these mice (see Example).

Importantly, the Inventors have selected antisense RNAs, in particular siRNAs, allowing inhibiting only partially, preferably from 40% to 60%, the expression of PMP22, in order to counteract the 50% overexpression of PMP22 due to 1.5 Mb duplication on chromosome 17p11.2. The protein PMP22 must indeed remain in the cells in an amount equivalent to those found in healthy individuals.

Moreover, to demonstrate that the siRNA PMP22 tightly regulate PMP22 expression the Inventors have shown that administration of an siRNA targeting PMP22 gene to wild-type mice decreased PMP22 protein level thus, inducing neuropathy in these mice (data not shown).

The antisense RNAs according to the invention, in particular the siRNAs PMP22, advantageously do not interfere with the expression of protein P0, which remains unchanged. Protein P0 is indeed involved with PMP22 in the myelination process and a deregulation of the gene encoding the protein P0 is responsible of another type of CMT such as CMT1B.

Importantly, the antisense RNAs according to the invention, in particular the siRNAs PMP22, do not affect the viability of cells.

To protect and safely deliver the antisense RNAs targeting PMP22, in particular the siRNAs targeting PMP22, they may be vectorized and for example be provided in the form of nanoparticles. For example, the antisense RNA may be conjugated to squalene, thereby forming nanoparticles comprising the antisense RNA. These nanoparticles (also referred to as siRNA PMP22-SQ NPs) are still active after bio-conjugation with squalene, thanks to modification only in the passenger sense strand. Advantageously, these nanoparticles are stable for 30 days with a size of around 180 nm and a low polydispersity index of 0.14, thereby allowing to be injected intravenously.

Whereas most drugs assessed for the treatment of CMT-1A focus on the adenylyl cyclase activity, which indirectly affects PMP22 expression, the antisense RNAs according to the invention, in particular the siRNAs, target the PMP22 gene itself and allow improving the different aspects of the disease, such as motor activity, strength and axonal regeneration.

Importantly, the therapeutic effect of the antisense RNAs provided by the present invention, in particular the siRNAs, has been demonstrated on an animal model close to human CMT-1A (in particular in mice having only one or two extra copies of the PMP22 gene) and in conditions transposable in human beings, in particular using an intravenous administration of a low dose of antisense RNA (for example 2.5 mg/kg). Administering a high dose of siRNA can indeed induce off-target effects. Besides, the antisense RNAs according to the invention provides a long-term therapeutic effect.

A first object of the invention is thus an antisense RNA targeting an mRNA encoding PMP22 protein.

The antisense RNA preferably reduces from 40% to 60% the amount of PMP22 protein in cells, more preferably from 40% to 55%.

The antisense RNA may be selected from the group consisting of a siRNA, shRNA, miRNA, dsRNA and a RNA species that can be cleaved in vivo to form an siRNA.

The antisense RNA may be complementary to a portion of (i) sequence SEQ ID NO: 9, (ii) SEQ ID NO: 11 or (iii) a naturally occurring variant of sequence SEQ ID NO: 9 or 11.

For example, the antisense RNA may be a nucleic acid complementary to:
 (i) a portion consisting of, comprised within or overlapping with:
  nucleotides 989 to 1007 of sequence SEQ ID NO: 11,
  nucleotides 970 to 988 of sequence SEQ ID NO: 9,
  nucleotides 1721 to 1739 of sequence SEQ ID NO: 11,
  nucleotides 1726 to 1744 sequence SEQ ID NO: 9,
  nucleotides 431 to 449 of sequence SEQ ID NO: 11, nucleotides 429 to 447 sequence SEQ ID NO: 9,
nucleotides 1805 to 1823 of sequence SEQ ID NO: 11,
nucleotides 1809 to 1827 sequence SEQ ID NO: 9,
nucleotides 921 to 939 of sequence SEQ ID NO: 11, or
nucleotides 903 to 921 sequence SEQ ID NO: 9, or
(ii) a portion homologous to a portion of (i) present in a naturally occurring variant.

The antisense RNA may comprise at least 10 consecutive nucleotides of a sequence selected from the group consisting of sequence SEQ ID NO: 15, SEQ ID NO: 16, SEQ ID NO: 17, SEQ ID NO: 18 and SEQ ID NO: 19.

The antisense RNA may be an siRNA comprising one or two single-stranded overhang(s), for example two single-stranded 3'-overhangs.

The antisense RNA may be an siRNA comprising or consisting of (i) a sequence selected from the group consisting of sequence SEQ ID NO: 15, SEQ ID NO: 16, SEQ ID NO: 17, SEQ ID NO: 18 and SEQ ID NO: 19 and (ii) optionally, one or two single-stranded overhang(s), in particular one or two single-stranded 3'-overhang(s).

Another object of the invention is a nanoparticle comprising an antisense RNA as defined above, wherein the antisense RNA is preferably coupled to squalene or a derivative thereof. The nanoparticle for example comprises a siRNA, wherein the sense strand of said siRNA is preferably coupled to squalene or a derivative thereof.

Another object of the invention is a pharmaceutical composition comprising or consisting of an antisense RNA targeting an mRNA encoding PMP22 protein as defined above and a pharmaceutically acceptable carrier.

The pharmaceutically acceptable carrier may be conjugated with the antisense RNA, for example with the sense strand of the antisense RNA. Such a pharmaceutically acceptable carrier may be a precursor of cholesterol, such as squalene, PEG, a phospholipid or a lipophilic moiety.

Still another object of the invention is an antisense RNA targeting an mRNA encoding PMP22 protein as defined above, for use in the treatment of Charcot-Marie-Tooth 1A (CMT-1A). The antisense RNA thus allows restoring a normal level of PMP22 expression in patients suffering from Charcot Marie Tooth disease 1A.

The antisense RNA may be provided in the form of nanoparticles comprising the said antisense RNA, for example nanoparticles as defined above.

The antisense RNA may be provided in the form a pharmaceutical composition as defined above.

The antisense RNA may be administered intravenously, intraperitoneally, subcutaneously or intranervously, for example in the sciatic nerve.

The antisense RNA may be used in combination with at least another drug useful in the treatment of Charcot-Marie-Tooth 1A.

PMP22 Protein

PMP22 protein, also called peripheral myelin protein 22, is a transmembrane glycoprotein.

Human PMP22 protein is encoded by the PMP22 gene.
PMP22 protein is mainly expressed in Schwann cells.
The PMP22 protein is preferably of mammalian origin.
The term "mammalian" includes human and non-human mammalian.
The expression "non-human mammalian" for example includes rat, murine, pig, cat, dog, rabbit or primate.

Charcot-Marie-Tooth 1A (CMT1A) disease results from a 1.5 Mb duplication on chromosome 17p11.2, containing the PMP22 coding gene, resulting in the presence of three copies of PMP22 in all individuals with CMT1A.

The PMP22 protein involved in CMT1A disease is a functional PMP22 protein.

By "functional PMP22 protein", it is herein meant a protein encoded by a gene able to increase PMP22 expression (if a duplication occurs at DNA level) on both mRNA level (for example tested by real-time polymerase chain reaction after RNA extraction followed by reverse transcription (RT-qPCR)) and protein level (for example tested by Western blot and by immunohistochemistry) leading to demyelination.

The skilled person can easily determine if a given PMP22 protein is functional by well-known methods. For example, the proband of the family history combined with very slow nerve conduction velocities may be used, or DNA diagnostics, RT-qPCR, Western Blot and/or electrophysiological tests.

A reference sequence for human PMP22 is for example sequence SEQ ID NO: 10.

The PMP22 protein may comprise or consist of a sequence at least 80% identical to sequence SEQ ID NO: 10, preferably at least 85% identical, more preferably at least 90% identical, more preferably at least 95% identical, for example at least 96%, at least 97%, at least 98% or at least 99% identical to sequence SEQ ID NO: 10.

A reference sequence for the mRNA encoding human PMP22 is sequence SEQ ID NO: 9, wherein nucleotides "T" are replaced with "U".

The mRNA encoding a human PMP22 protein may comprise or consist of a sequence at least 80% identical to sequence SEQ ID NO: 9, wherein nucleotides "T" are replaced with "U", preferably at least 85% identical, more preferably at least 90% identical, more preferably at least 95% identical, for example at least 96%, at least 97%, at least 98% or at least 99% identical to sequence SEQ ID NO: 9, wherein nucleotides "T" are replaced with "U".

A reference sequence for the mRNA encoding murine PMP22 is sequence SEQ ID NO: 11, wherein nucleotides "T" are replaced with "U".

The mRNA encoding a murine PMP22 protein may comprise or consist of a sequence at least 80% identical to sequence SEQ ID NO: 11, wherein nucleotides "T" are replaced with "U", preferably at least 85% identical, more preferably at least 90% identical, more preferably at least 95% identical, for example at least 96%, at least 97%, at least 98% or at least 99% identical to sequence SEQ ID NO: 11, wherein nucleotides "T" are replaced with "U".

As defined herein, an amino acid sequence "at least 80%, 85%, 90%, 95%, 96%, 97%, 98% or 99% identical" to a reference sequence may comprise mutation(s), such as deletion(s), insertion(s) and/or substitution(s) compared to the reference sequence.

In case of substitution, the substitution preferably corresponds to a conservative substitution as indicated in the Table 1 below. In a preferred embodiment, the sequence at least 80%, 85%, 90%, 95%, 96%, 97%, 98% or 99% identical to a reference sequence only differs from the reference sequence by conservative substitutions.

TABLE 1

| Conservative substitutions | Type of Amino Acid |
|---|---|
| Ala, Val, Leu, Ile, Met, Pro, Phe, Trp | Amino acids with aliphatic hydrophobic side chains |
| Ser, Tyr, Asn, Gln, Cys | Amino acids with uncharged but polar side chains |

TABLE 1-continued

| Conservative substitutions | Type of Amino Acid |
|---|---|
| Asp, Glu | Amino acids with acidic side chains |
| Lys, Arg, His | Amino acids with basic side chains |
| Gly | Neutral side chain |

The amino acid sequence at least 80%, 85%, 90%, 95%, 96%, 97%, 98% or 99% identical to a reference sequence may correspond to a naturally-occurring variant of the reference sequence.

The amino acid sequence at least 80%, 85%, 90%, 95%, 96%, 97%, 98% or 99% identical to a reference sequence may correspond to a homologous sequence derived from another mammalian species than the reference sequence.

For example, the amino acid sequence at least 80%, 85%, 90%, 95%, 96%, 97%, 98% or 99% identical to a reference sequence may differ from the reference sequence by conservative substitution(s) and/or corresponds to a naturally-occurring variant of the reference sequence and/or corresponds to a homologous sequence derived from another mammalian species than the reference sequence.

By "a sequence at least x % identical to a reference sequence", it is intended that the sequence is identical to the reference sequence or differ from the reference sequence by up to 100-x amino acid alterations per each 100 amino acids of the reference sequence.

The alignment and the determination of the percentage of identity may be carried out manually or automatically using for instance the Needle program which is based on the Needleman and Wunsch algorithm, described in Needleman and Wunsch (1970) J. Mol Biol. 48:443-453, with for example the following parameters for polypeptide sequence comparison: comparison matrix: BLOSUM62, gap open penalty: 10 and gap extend penalty: 0.5, end gap penalty: false, end gap open penalty=10, end gap extend penalty=0.5; and the following parameters for polynucleotide sequence comparison: comparison matrix: DNAFULL; gap open penalty=10, gap extend penalty=0.5, end gap penalty: false, end gap open penalty=10, end gap extend penalty=0.5.

A nucleic sequence "at least 80%, 85%, 90%, 95%, 96%, 97%, 98% or 99% identical" to a reference sequence may comprise mutation(s), such as deletion(s), insertion(s) and/or substitution(s) compared to the reference sequence.

In case of nucleotide substitution, the substitution may correspond to a silent substitution or a substitution leading to a conservative substitution in the translated amino acid sequence, by comparison to the reference sequence, for example as indicated in the Table 1 above.

The nucleic sequence at least 80%, 85%, 90%, 95%, 96%, 97%, 98% or 99% identical to a reference sequence may correspond to a naturally-occurring variant of the reference sequence and/or corresponds to a homologous sequence derived from another mammalian species than the reference sequence.

The nucleic sequence at least 80%, 85%, 90%, 95%, 96%, 97%, 98% or 99% identical to a reference sequence may differs from the reference sequence by silent substitution(s) and/or substitution(s) leading to a conservative amino-acid substitution and/or correspond to a naturally-occurring variant of the reference sequence and/or corresponds to a homologous sequence derived from another mammalian species than the reference sequence.

Antisense RNA Targeting an mRNA Encoding PMP22 Protein

The present invention particularly relates to an antisense RNA targeting an mRNA encoding PMP22 protein.

The PMP22 protein and the mRNA encoding PMP22 are particularly as defined above.

The antisense RNA targeting an mRNA encoding PMP22 protein is referred to as "antisense RNA" in the following.

The antisense RNA advantageously reduces the amount of PMP22 protein in cells, in particular in Schwann cells.

The antisense RNA preferably reduces from 40% to 60%, preferably from 40% to 55%, more preferably from 40% to 50%, for example from 40% to 45% or from 45% to 50%, the amount of PMP22 protein in a cell, preferably in a Schwann cell, and/or reduces from 40% to 60%, preferably from 40% to 55%, preferably from 40% to 50%, for example from 40% to 45% or from 45% to 50%, the amount of PMP22 mRNA in a cell, preferably in a Schwann cell.

The quantity of PMP22 protein expressed in a cell may be determined by any method well known by the skilled person, such as Western blot, Elisa (enzyme-linked immunosorbent assay) or immunohistochemistry.

Determining whether an antisense RNA is capable of reducing the amount of PMP22 in cells and, optionally, to quantify the percentage of reduction may for example be performed by assessing the amount of PMP22 protein in a cell in the presence and in the absence of the antisense RNA to be tested (see for example in the section Example).

The quantity of mRNA encoding PMP22 present in a cell may be determined by any method well known by the skilled person, such as RT-PCR.

Determining whether an antisense RNA is capable of reducing the amount of mRNA encoding PMP22 in cells and, optionally, to quantify the percentage of reduction may for example be performed by assessing the amount of mRNA encoding PMP22 in cells, for example by RT-PCR, in the presence and absence of the antisense RNA to be tested (see for example in the section Example).

The antisense RNA is thus a nucleic acid targeting an mRNA encoding PMP22.

The expression "nucleic acid targeting a given mRNA" herein means a nucleic acid that is capable of specifically binding to the said mRNA. The nucleic acid targeting a given mRNA thus comprises or consists of a sequence that is perfectly complementary to a portion of the sequence of said mRNA. Said complementarity enables specific binding of the nucleic acid targeting the mRNA to said mRNA under intra-cellular conditions.

By the expression "a sequence perfectly complementary to a second sequence", it is herein meant the reverse complement counterpart of the second sequence.

The antisense RNA targeting an mRNA encoding PMP22 may be designed from the sequence of said mRNA, for example using bioinformatic tools. For example, sequences SEQ ID NO: 9 or SEQ ID NO: 11 can be used as target for designing the antisense RNA. Since sequences SEQ ID NO: 9 and SEQ ID NO: 11 are cDNA sequences, nucleotides "T" have to be replaced with nucleotides "U" to get the mRNA sequence.

The antisense RNA as defined above may be a single-stranded or double-stranded RNA (ribonucleic acid), such as siRNA.

The antisense RNA is preferably perfectly complementary to a portion of the sequence of the mRNA encoding PMP22 in the subject to be treated.

The antisense RNA as defined above may comprise at least one non-standard nucleotide, such as a non-naturally occurring nucleotide or a deoxyribonucleotide.

The antisense RNA as defined above may comprise or consist of an RNA portion and at least one additional portion, for example a deoxyribonucleotide portion.

The antisense RNA as defined above may have a length of from 12 to 50 nucleotides, 12 to 35 nucleotides, from 12 to 30, from 12 to 25, from 12 to 22, from 15 to 35, from 15 to 30, from 15 to 25, from 15 to 22, or from 18 to 22, for example of 19, 20 or 21 nucleotides.

The antisense RNA as defined above may for example comprise or consist of 12 to 50 consecutive nucleotides, 12 to 35, from 12 to 30, from 12 to 25, from 12 to 22, from 15 to 35, from 15 to 30, from 15 to 25, from 15 to 22 or from 18 to 22, for example 19, 20 or 21 nucleotides.

The antisense RNA as defined above may comprise or consist of 12 to 50 consecutive nucleotides, e.g. 12 to 35, from 12 to 30, from 12 to 25, from 12 to 22, from 15 to 35, from 15 to 30, from 15 to 25, from 15 to 22 or from 18 to 22, for example 19, 20 or 21 consecutive nucleotides of a sequence complementary to the mRNA encoding PMP22 protein.

The antisense RNA is preferably a RNA interfering agent.

The antisense RNA as defined above, in particular the RNA interfering agent, may be selected from the group consisting of a siRNA, shRNA, miRNA, dsRNA and an RNA species that can be cleaved in vivo to form a siRNA.

A "short interfering RNA" or "siRNA" comprises a double-stranded RNA portion and, optionally, one or two single-stranded overhangs.

The single-stranded overhang may be a 3' overhang or a 5' overhang.

The double-stranded RNA portion comprises an antisense strand complementary to the mRNA encoding PMP22 protein and a sense strand.

The siRNA as defined above preferably comprises one or two 3' overhangs.

The siRNA as defined above preferably comprises or consists of 19, 20 or 21 base pairs.

The siRNA as defined above preferably comprises or consists of 19, 20 or 21 base pairs and two 3' overhangs.

The 3' and/or 5' overhang may consist of at least one, preferably at least two deoxyribonucleotides T (referred to as "dT").

For example, the 3' and/or 5' overhang(s) may consist of two deoxyribonucleotides T.

A "short hairpin RNA (shRNA)" is a single-stranded RNA having a stem-loop (hairpin) structure. Expression of shRNA in cells may be obtained using a vector.

A "MicroRNA" or "miRNA" is a short non-coding RNA of around 22-nucleotide length-miRNAs are post-transcriptional regulators of target genes and are generally expressed in a highly tissue-specific or developmental-stage-specific fashion. It is possible to design and express an artificial miRNA based on the features of existing miRNA genes.

A "dsRNA" is a RNA with double strands same as the DNA but with uracil instead of thymine. It forms the genetic material of many viruses, it is a main component of the interferon system. It triggers the immune system against viral infection.

The antisense RNA as defined above may target a portion of sequence SEQ ID NO: 9, of sequence SEQ ID NO: 11, or of a naturally occurring variant thereof, wherein nucleotides "T" are replaced with nucleotides "U" in these sequences.

In other words, the antisense RNA as defined above may be complementary to a portion of (i) sequence SEQ ID NO: 9, (ii) SEQ ID NO: 11 or (iii) a naturally occurring variant of sequence SEQ ID NO: 9 or 11.

An antisense RNA complementary to a portion of a sequence which is a DNA sequence herein means that it is complementary to the corresponding RNA sequence, wherein nucleotides "T" in the DNA sequence are replaced with nucleotides "U".

The antisense RNA as defined above may target a portion of a sequence at least 80% identical to sequence SEQ ID NO: 9, preferably at least 85% identical, more preferably at least 90% identical, more preferably at least 95% identical, for example at least 96%, at least 97%, at least 98% or at least 99% identical to sequence SEQ ID NO: 9, the nucleotides "T" being considered identical to nucleotides "U" for determining sequence identity.

In other words, the antisense RNA as defined above may target a portion of a sequence at least 80% identical to sequence SEQ ID NO: 11, preferably at least 85% identical, more preferably at least 90% identical, more preferably at least 95% identical, for example at least 96%, at least 97%, at least 98% or at least 99% identical to sequence SEQ ID NO: 11.

The antisense RNA as defined above may be complementary to:
(i) a portion consisting of, comprised within or overlapping with:
  nucleotides 989 to 1007 of sequence SEQ ID NO: 11,
  nucleotides 970 to 988 of sequence SEQ ID NO: 9,
  nucleotides 1721 to 1739 of sequence SEQ ID NO: 11,
  nucleotides 1726 to 1744 sequence SEQ ID NO: 9,
  nucleotides 431 to 449 of sequence SEQ ID NO: 11,
  nucleotides 429 to 447 sequence SEQ ID NO: 9,
  nucleotides 1805 to 1823 of sequence SEQ ID NO: 11,
  nucleotides 1809 to 1827 sequence SEQ ID NO: 9,
  nucleotides 921 to 939 of sequence SEQ ID NO: 11, or
  nucleotides 903 to 921 sequence SEQ ID NO: 9, or
(ii) a portion homologous to a portion of (i) present in a naturally occurring variant.

The antisense RNA as defined above may comprise at least 10 consecutive nucleotides, preferably at least 12 nucleotides, more preferably at least 15 nucleotides, for example 16, 17, 18 or 19 nucleotides, of a sequence selected from the group consisting of sequence SEQ ID NO: 15, SEQ ID NO: 16, SEQ ID NO: 17, SEQ ID NO: 18 and SEQ ID NO: 19.

The antisense RNA as defined above may be an siRNA comprising (i) at least 10 consecutive nucleotides, preferably at least 12 nucleotides, more preferably at least 15 nucleotides, for example 16, 17, 18 or 19 nucleotides, of a sequence selected from the group consisting of sequence SEQ ID NO: 15, SEQ ID NO: 16, SEQ ID NO: 17, SEQ ID NO: 18 and SEQ ID NO: 19 and (ii) optionally, one or two single-stranded overhang(s), said 3' or 5' overhang(s) consisting for example of two dT.

The antisense RNA as defined above, preferably a siRNA, may comprise or consist of (i) a sequence selected from the group consisting of sequence SEQ ID NO: 15, SEQ ID NO: 16, SEQ ID NO: 17, SEQ ID NO: 18 and SEQ ID NO: 19 and (ii) optionally, one or two single-stranded overhang(s), said 3' and/or 5' overhang(s) consisting for example of two dT.

The antisense RNA as defined above is preferably a siRNA comprising or consisting of (i) a sequence selected from the group consisting of sequence SEQ ID NO: 15, SEQ ID NO: 16, SEQ ID NO: 17, SEQ ID NO: 18 and SEQ ID NO: 19, and (ii) two 3' overhangs, each of said 3' overhangs consisting preferably of two dT.

The antisense RNA as defined above may comprise modified nucleotides, for example chemically modified nucleotides, in order to increase its stability and/or therapeutic efficiency in vivo.

For example, the antisense RNA as defined above may comprise phosphorothioate derivatives, 2'-O-(2-methoxyethyl) oligoribonucleotides and/or lipid-modified oligonucleotides. When the antisense RNA comprises a double-stranded RNA portion, the sense strand (also called passenger strand) may comprise the same modification(s) as the antisense strand, so that the modification(s) will not affect the inhibitory effect of the antisense strand. Alternatively, when the antisense RNA comprises a double-stranded RNA portion, only the sense strand may comprise modification(s), such as for example a dibenzocyclooctyne (DBCO) reactive group at the 5'-end of the sense strand, in particular through a spacer, such as a N-(hexamethylenyl)-6-oxohexanamide spacer (C6).

The antisense RNA as defined above, in particular the shRNA, may be cloned into a vector and then transmitted to cells.

The antisense RNA as defined above may be provided in a pharmaceutical composition.

Nanoparticle Comprising at Least One Antisense RNA

The antisense RNA as defined above may be provided in the form of a nanoparticle comprising the said antisense RNA.

The nanoparticle may be loaded with the antisense RNA.

Using nanoparticles enables to increase the half-life of the antisense RNA, in particular in the case of an siRNA.

Besides, nanoparticles may allow specific delivery to target cells, for example by targeting intrinsically the target cells or by being coupled to a ligand specific to the target cells.

Target cells are for example Schwann cells.

For example, natural triterpenes, such as squalene, have the ability when linked to a siRNA to self-assemble as nanoparticles in water.

Vectorization with squalenic acid or a derivative thereof is for example disclosed in document WO2006/090029.

In one advantageous embodiment, the sense strand of a siRNA is covalently coupled to azide squalene or a derivative thereof, that is further annealed to the antisense strand of said siRNA; thereby forming nanoparticles, in particular after nanoprecipitation.

The sense strand of the antisense RNA as defined above, in particular of the siRNA as defined above, may be coupled to squalene by using copper-free click chemistry, for example as previously described (Massaad-Massade et al., Bioconjugate Chem., 2018, 29 (6), pp 1961-1972, DOI: 10.1021/acs.bioconjchem.8b00205).

A nanoparticle comprising an siRNA as defined above may be obtained by a method comprising:
- adding a dibenzocyclooctyne residue to the 5'-end of the sense strand of the siRNA, to obtain a modified sense strand,
- coupling squalene to the said modified sense strand, in particular via bioconjugation of the azide functional group of the squalene to the dibenzocyclooctyne residue,
- adding the antisense strand of the siRNA, for annealing both strands of the siRNA,
- optionally, adding acetone and water to precipitate the nanoparticles, in particular by adding slowly one phase (aqueous or organic) to the other, preferably under stirring, and
- optionally, evaporating acetone, for example using nitrogen flux, to obtain an aqueous suspension of pure siRNA-SQ nanoparticles.

The nanoparticle may be purified, for example by HPLC.

The nanoparticles preferably have a size lower than 300 nm, more preferably lower than 250 nm and/or a size greater than 50 nm, more preferably greater than 100 nm.

For example, the nanoparticles have a size comprised from 100 to 200 nm, more preferably from 170 nm to 190 nm, for example 180 nm.

The nanoparticles preferably have a low polydispersity index, in particular a polydispersity lower than 0.3 nm, more preferably lower than 0.2 nm, for example a polydispersity index of 0.14.

The nanoparticles are preferably stable for at least 20 days, preferably at least 25 days, more preferably at least 30 days.

The nanoparticles are preferably suitable for intravenous injection.

The nanoparticle may particularly comprise an siRNA comprising or consisting of (i) a sequence selected from the group consisting of sequence SEQ ID NO: 15, SEQ ID NO: 16, SEQ ID NO: 17, SEQ ID NO: 18 and SEQ ID NO: 19 and (ii) two 3' overhangs, said 3' overhangs preferably consisting of two dT.

The nanoparticle comprising the antisense RNA may be provided in a pharmaceutical composition.

Pharmaceutical Composition

The present invention also relates to a pharmaceutical composition comprising or consisting of an antisense RNA targeting an mRNA encoding PMP22 protein as defined above, in particular an siRNA targeting an mRNA encoding PMP22 protein as defined above, and a pharmaceutically acceptable carrier.

Non-limiting examples of a pharmaceutically acceptable carrier that may be conjugated with a nucleic acid such as an antisense RNA, for example with the sense strand of a siRNA, include: a precursor of cholesterol, such as squalene, PEG, phospholipid, lipophilic moiety, P-glycoprotein inhibitor.

The antisense RNA can thus be provided in the form of an exosome comprising or conjugated with the nucleic acid, liposome comprising or conjugated with the nucleic acid and/or nanoparticle comprising or conjugated with the nucleic acid, for example a nanoparticle as defined above.

The expression "pharmaceutically acceptable" is meant to encompass any carrier, which does not interfere with the effectiveness of the biological activity of the active ingredient and that is preferably not toxic to the host to which is administered.

A pharmaceutically acceptable carrier can be prepared by any method known by those skilled in the art.

The pharmaceutical composition is preferably a sterile solution or suspension.

The pharmaceutical composition is preferably suitable for injectable administration.

The pharmaceutical composition may comprise a nucleic acid encoding the antisense RNA in case of siRNA or a vector comprising the said nucleic acid, in particular when the antisense RNA is a part of shRNA.

The pharmaceutical composition may further comprise at least one pharmaceutically acceptable excipient.

Suitable pharmaceutically acceptable excipients are well known by the skilled person. Pharmaceutically acceptable excipients can be routinely selected in accordance with the mode of administration, solubility and stability of the RNA antisense. For example, a pharmaceutical composition for intravenous administration may include a sterile aqueous solution, buffer, diluent and/or other suitable additive.

The pharmaceutical composition as defined above may comprise an amount of RNA antisense suitable for administering from 0.1 mg of RNA antisense/kg of the subject to 20 mg of RNA antisense/kg of the subject, preferably from 0.2 mg/kg to 15 mg/kg, more preferably from 0.5 mg/kg to 10 mg/kg.

The pharmaceutical composition as defined above may for example comprise from 5 mg to 2 g of RNA antisense/kg of the subject, preferably from 15 mg to 1 g, more preferably from 30 mg to 500 mg.

When the antisense RNA is coupled to squalene or a derivative thereof, thereby forming nanoparticles, the pharmaceutical composition as defined above may comprise an amount of nanoparticles suitable for administering from 0.1 mg of nanoparticles/kg of the subject to 20 mg of nanoparticles/kg of the subject, preferably from 0.2 mg/kg to 15 mg/kg, more preferably from 0.5 to 10 mg/kg.

When the antisense RNA is coupled to squalene or a derivative thereof, thereby forming nanoparticles, the pharmaceutical composition as defined above may comprise from 5 mg to 2 g of nanoparticles, preferably from 15 mg to 1 g, more preferably from 30 mg to 500 mg.

In one embodiment, the pharmaceutical composition is presented in unit dosage form to facilitate accurate dosing. The term "unit dosage form" refers to physically discrete unit suitable as unitary dosage for human subject and other non-human mammals, each unit containing a pre-determined quantity of active material calculated to produce the desired therapeutic effect, in association with a suitable pharmaceutical excipient. A typical unit dosage form includes pre-filled, pre-measured ampoules or syringes of the liquid composition.

The present invention also related to a kit comprising a pharmaceutical as defined above and instructions regarding the mode of administration. These instructions may for e.g. indicate the medical indication, the route of administration, the dosage and/or the group of patients to be treated.

Subject

The subject may be a human being or a non-human mammal.

A non-human mammal is for example a mouse, rat, cat, dog, rabbit or primate.

The subject is preferably a human being, also referred to as individual or patient.

The subject may be of any age, for example an infant, child, adolescent, adult, elderly people, and of any sex.

Treatment of Charcot-Marie-Tooth 1A Disease

By "treatment of Charcot-Marie-Tooth 1A disease", it is herein meant stopping, at least partially, the evolution of the disease or reversing the disease.

Desirable effects of treatment for example comprise:
preventing or reducing weakness and/or atrophy of the muscles of the lower legs, hand weakness and/or sensory loss, thereby normalizing gait and/or preventing or reducing foot drops,
stopping, slowing down or curing weakness and/or atrophy of the muscles of the lower legs, hand weakness and/or sensory loss, thereby normalizing gait and/or reducing foot drops, and/or
normalizing the nerve conduction velocity.

Antisense RNA Targeting PMP22 for Use in the Treatment of Charcot-Marie-Tooth 1A Disease The present invention also relates to an antisense RNA targeting an mRNA encoding PMP22 protein for use in the treatment of Charcot-Marie-Tooth 1A (CMT-1A).

The present invention also relates to a method for treating Charcot-Marie-Tooth 1A disease, comprising administering an antisense RNA targeting an mRNA encoding PMP22 protein to a subject in need thereof.

The antisense RNA targeting an mRNA encoding PMP22 is particularly as defined above.

The antisense RNA may be provided in the form of a pharmaceutical composition.

The pharmaceutical composition is particularly as defined above in the section of the same name.

The treatment of Charcot-Marie-Tooth 1A disease is particularly as defined above.

Administering an antisense RNA targeting an mRNA encoding PMP22, in particular a siRNA, may be carried out using various techniques well known in the art, including naked administration and/or administration in pharmaceutically acceptable carrier, such as a nanoparticle.

A nanoparticle comprising an antisense RNA according to the invention is particularly as defined above.

The antisense RNA may be formulated to target Schwann cells.

The antisense RNA is preferably complementary to the mRNA encoding PMP22 present in the subject suffering from or susceptible of suffering from CMT-1A.

The antisense RNA targeting an mRNA encoding PMP22 may for example be administered intravenously or intraperitoneally or subcutaneously or intranervously, preferably in the sciatic nerve.

The antisense RNA targeting an mRNA encoding PMP22 is preferably administered in an "effective amount", i.e. in an amount sufficient to treat the Charcot-Marie-Tooth 1A disease. It will be appreciated that this amount will vary both with the effectiveness of the antisense RNA and with the nature of any carrier used. The determination of appropriate amounts for any given composition is within the skill in the art, through standard series of tests designed to assess appropriate therapeutic levels.

The antisense RNA targeting an mRNA encoding PMP22 may be administered at a dose of 0.1 to 20 mg/kg of the subject, preferably 0.2 to 15 mg/kg of the subject, more preferably 0.5 to 10 mg/kg of the subject.

When the antisense RNA targeting an mRNA encoding PMP22 is coupled to a squalene or derivative thereof, 0.1 to 20 mg of nanoparticles/kg of the subject may be administered, preferably 0.2 to 15 mg of nanoparticles/kg of the subject, more preferably 0.5 to 10 mg of nanoparticles/kg of the subject.

The antisense RNA targeting an mRNA encoding PMP22 may be administered as one injection or several injections, for example once or twice per week, for example for at least three weeks and/or maximum 3 months.

The antisense RNA may be used in combination with at least another drug useful in the treatment of Charcot-Marie-Tooth 1A, such as ascorbic acid, neutrophin 3 and/or curcumin.

The present invention will be further illustrated in view of the following examples and figures.

BRIEF DESCRIPTION OF THE SEQUENCES

SEQ ID NO: 1 is the sense strand sequence of a siRNA comprising the antisense strand of SEQ ID NO: 12.

SEQ ID NO: 2 is the sense strand sequence of a siRNA comprising the antisense strand of SEQ ID NO: 13.

SEQ ID NO: 3 is the sense strand sequence of a siRNA comprising the antisense strand of SEQ ID NO: 14.

SEQ ID NO: 4 is the sense strand sequence of a siRNA comprising the antisense strand of SEQ ID NO: 15.

SEQ ID NO: 5 is the sense strand sequence of a siRNA comprising the antisense strand of SEQ ID NO: 16.

SEQ ID NO: 6 is the sense strand sequence of a siRNA comprising the antisense strand of SEQ ID NO: 17.

SEQ ID NO: 7 is the sense strand sequence of a siRNA comprising the antisense strand of SEQ ID NO: 18.

SEQ ID NO: 8 is the sense strand sequence of a siRNA comprising the antisense strand of SEQ ID NO: 19.

SEQ ID NO: 9 is the cDNA sequence encoding the human PMP22 protein of reference sequence NM_000304.3, as available on Jul. 30, 2018.

SEQ ID NO: 10 is the amino acid sequence of the human PMP22 protein encoded by sequence SEQ ID NO: 9.

SEQ ID NO: 11 is the cDNA sequence the sense strand is the cDNA encoding the murine PMP22 protein of reference NM_008885.3 in the NCBI database, as available on Jul. 30, 2018.

SEQ ID NO: 12 is a RNA sequence perfectly complementary to nucleotides 474 to 492 of sequence SEQ ID NO: 11 and partially complementary to nucleotides 472 to 489 of sequence SEQ ID NO: 9 (one mismatch with nucleotide 472).

SEQ ID NO: 13 is a RNA sequence perfectly complementary to nucleotides 923 to 941 of sequence SEQ ID NO: 11 and to nucleotides 905 to 923 sequence SEQ ID NO: 9.

SEQ ID NO: 14 is a RNA sequence perfectly complementary to nucleotides 1562 to 1580 of sequence SEQ ID NO: 11 and partially complementary to nucleotides 1565 to 1583 sequence SEQ ID NO: 9 (5 mismatches).

SEQ ID NO: 15 is a RNA sequence perfectly complementary to nucleotides 989 to 1007 of sequence SEQ ID NO: 11 and partially complementary to nucleotides 970 to 988 sequence SEQ ID NO: 9 (2 mismatches).

SEQ ID NO: 16 is a RNA sequence perfectly complementary to nucleotides 1721 to 1739 of sequence SEQ ID NO: 11 and perfectly complementary to nucleotides 1726 to 1744 sequence SEQ ID NO: 9.

SEQ ID NO: 17 is a RNA sequence perfectly complementary to nucleotides 431 to 449 of sequence SEQ ID NO: 11 and perfectly complementary to nucleotides 429 to 447 sequence SEQ ID NO: 9.

SEQ ID NO: 18 is a RNA sequence perfectly complementary to nucleotides 1805 to 1823 of sequence SEQ ID NO: 11 and perfectly complementary to nucleotides 1809 to 1827 sequence SEQ ID NO: 9.

SEQ ID NO: 19 is a RNA sequence perfectly complementary to nucleotides 921 to 939 of sequence SEQ ID NO: 11 and perfectly complementary to nucleotides 903 to 921 sequence SEQ ID NO: 9.

EXAMPLES

Figure 1:
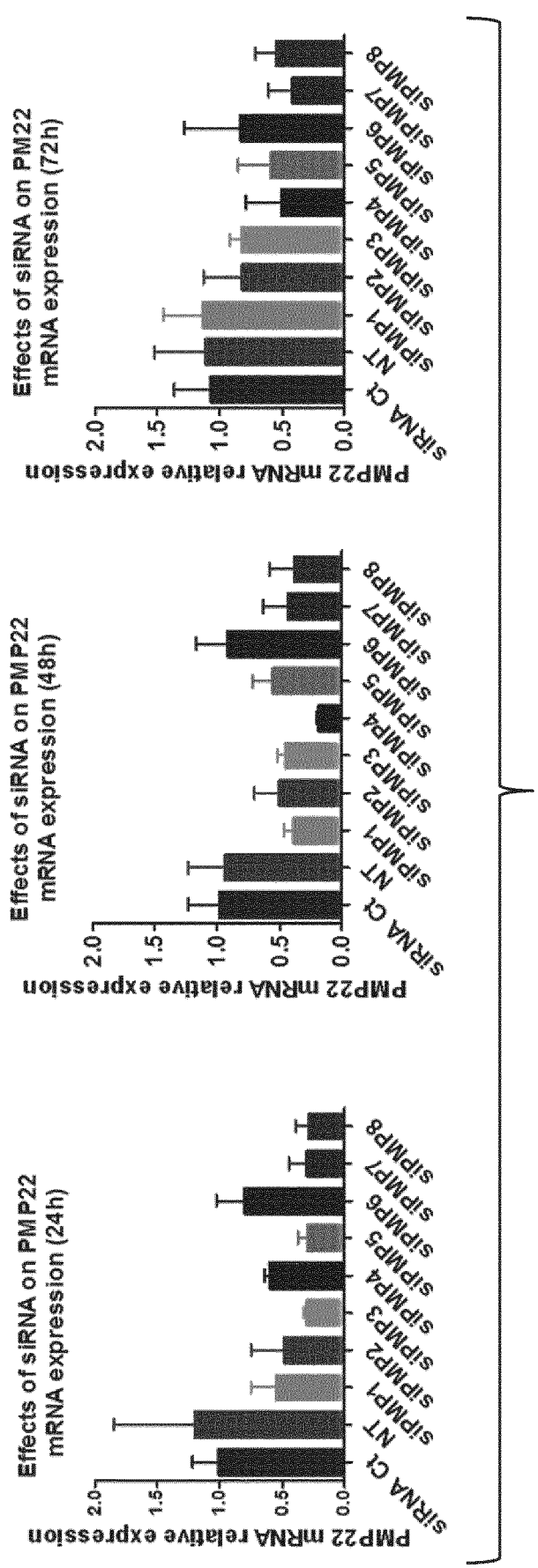
FIG. 1: Effect of siRNAs PMP22 on PMP22 gene expression. By using Kruskal-Wallis analysis followed by Dunns tests a statistical difference was found between siRNAs PMP22 (from 1 to 8) and siRNA control (CT). A statistical difference between siRNAs PMP22 (from 1 to 8) and non-treated cells (NT) was also found.

Materials and Methods
siRNAs and Chemical Modifications

The designed sequences of sense and antisense siRNA strands were purchased from Eurogentec, France. They were synthesized then characterized by matrix assisted laser desorption/ionization time-of-flight mass spectrometry (MALDI-TOF MS) and purified by Reverse Phase-high performance liquid chromatography (RP-HPLC). Single-stranded RNAs were synthesized as 19-mers with two 3'-overhanging 2'-deoxynucleotides residues to provide stabilization against nucleases. To preserve the functionality, a dibenzocyclooctyne (DBCO) reactive group was introduced at the 5'-end of the sense strand of each siRNA sequence through a N-(hexamethylenyl)-6-oxohexanamide spacer (C6). To generate siRNA from RNA single strands, equimolar amounts of both sense and antisense strands were annealed in annealing buffer [30 mM HEPES-KOH (pH 7.4), 2 mM Mg acetate, 100 mM K acetate] for 3 min at 95° C. and then incubated for 45 min at room temperature before storing at −20° C.

Screening of siRNA Against PMP22

To restore basal levels of PMP22 gene expression, eight siRNAs against PMP22 (see Tables 2 and 3) and an siRNA control (siRNA CTRL) scrambled sequence were designed by using three different methods (Tafer software, Thermofisher software and Reynold method). siRNAs were transfected by using lipofectamine MAX® into a Schwann cellular model (MSC 80) that endogenously express PMP22. The ability of the siRNAs to decrease the PMP22 expression was tested at 24 h, 48 h and 72 h. Expression of both PMP22 and P0 genes was assessed by real-time PCR. Then the best siRNA sequence that was able to inhibit of about 50% PMP22 expression with a long lasting-effect without affecting P0 level (P0 deregulation is described to be involve in the CMT-1 disease) was tested at different concentrations 25 nM, 50 nM and 100 nM to check its ability to decrease PMP22 and cell viability (MTT test). Scramble siRNA was used as control.

TABLE 2

Sequence and position of the siRNAs

| no of siRNA | Corresponding sequence | Position within SEQ ID NO: 11 (murine PMP22 cDNA) | SEQUENCE (ANTISENS) |
|---|---|---|---|
| 1 | SEQ ID NO: 1 | siPMP22 474-492 | GGCUCUGUUCCUGUUCUUC[dT][dT] |
|   | SEQ ID NO: 12 | siPMP22 474-492_as | GAAGAACAGGAACAGAGCC[dT][dT] |
| 2 | SEQ ID NO: 2 | siPMP22 923-941 | ACCUAUUUAUAACACUUUU[dT][dT] |
|   | SEQ ID NO: 13 | siPMP22 923-941_as | AAAAGUGUUAUAAAUAGGU[dT][dT] |
| 3 | SEQ ID NO: 3 | siPMP22 1562-1580 | ACAAUAAAUAAAUCUCAAA[dT][dT] |
|   | SEQ ID NO: 14 | siPMP22 1562-1580_as | UUUGAGAUUUAUUUAUUGU[dT][dT] |
| 4 | SEQ ID NO: 4 | siPMP22 989-1007 | CCUCGUGUUGAAUCUUAAA[dT][dT] |
|   | SEQ ID NO: 15 | siPMP22 989-1007_as | UUUAAGAUUCAACACGAGG[dT][dT] |
| 5 | SEQ ID NO: 5 | siPMP22 1721-1739 | CCACCAACUGUAGAUGUAU[dT][dT] |
|   | SEQ ID NO: 16 | siPMP22 1721-1739_as | AUACAUCUACAGUUGGUGG[dT][dT] |
| 6 | SEQ ID NO: 6 | siPMP22 431-449 | CUGUCCAGGCCACCAUGAU[dT][dT] |
|   | SEQ ID NO: 17 | siPMP22 431-449_as | AUCAUGGUGGCCUGGACAG[dT][dT] |
| 7 | SEQ ID NO: 7 | siPMP22 1805-1823 | AUACCAACUGUGUGGACUA[dT][dT] |
|   | SEQ ID NO: 18 | siPMP22 1805-1823_as | UAGUCCACACAGUUGGUAU[dT][dT] |
| 8 | SEQ ID NO: 8 | siPMP22 921-939 | AAACCUAUUUAUAACACUU[dT][dT] |
|   | SEQ ID NO: 19 | siPMP22 921-939_as | AAGUGUUAUAAAUAGGUUU[dT][dT] |

TABLE 3

Design of siRNAs targeting PMP22. The Table shows the sequences of 8 different siRNAs and their corresponding calculated "Reynolds scores" (according to Reynolds and Tafer, Nature biotech., 2008, (26) 5, 578-83). Highly efficient siRNA should have a score > 6.

| no of siRNA | Corresponding sequence | Score | | | | | | | | Total |
|---|---|---|---|---|---|---|---|---|---|---|
|   |   | 1 | 2 | 3 | 4 | 5 | 6 | 7 | 8 |   |
| 1 | sense SEQ ID NO: 1 antisense SEQ ID NO: 12 | 1 | 3 | 1 | 0 | 0 | 0 | −1 | −1 | 3 |
| 2 | sense SEQ ID NO: 2 antisense SEQ ID NO: 13 | 0 | 4 | 1 | 0 | 0 | 1 | 0 | 0 | 6 |
| 3 | sense SEQ ID NO: 3 antisense SEQ ID NO: 14 | 0 | 3 | 0 | 1 | 1 | 0 | 0 | 0 | 5 |
| 4 | sense SEQ ID NO: 4 antisense SEQ ID NO: 15 | 1 | 5 | 1 | 1 | 0 | 0 | 0 | 0 | 8 |
| 5 | sense SEQ ID NO: 5 antisense SEQ ID NO: 16 | 1 | 3 | 0 | 0 | 1 | 0 | 0 | 0 | 5 |
| 6 | sense SEQ ID NO: 6 antisense SEQ ID NO: 17 | 0 | 4 | 0 | 0 | 0 | 0 | 0 | 0 | 4 |
| 7 | sense SEQ ID NO: 7 antisense SEQ ID NO: 18 | 1 | 3 | 1 | 1 | 1 | 0 | 0 | 0 | 7 |
| 8 | sense SEQ ID NO: 8 antisense SEQ ID NO: 19 | 0 | 3 | 0 | 0 | 1 | 1 | 0 | 0 | 5 |

Conjugation of siRNA to Squalene and Polyisoprenyl Chains:

Squalene was coupled to siRNA by a Huisgen cycloaddition of dibenzocyclooctyne (copper-free click chemistry) as previously described (Massaad-Massade et al., Bioconjugate Chem., 2018, 29 (6), pp 1961-1972, DOI: 10.1021/acs.bioconjchem.8b00205). Briefly, the sense strands of the oligonucleotides were modified by dibenzocyclooctyne residue at the 5'-end, a commercially available modification for siRNAs. Squalene is carrying an azide functional group. The conjugates were purified by HPLC and characterized by MALDI-TOFF mass spectrometry.

Annealing of both strands of the siRNA PMP22 and siRNA CT was performed after the bioconjugation of the sense strand to SQ, then precipitated in acetone/water. One phase (aqueous or organic) was slowly added to the other, under stirring. Acetone was completely evaporated using nitrogen flux to obtain an aqueous suspension of pure siRNA-SQ nanoassemblies at 10 µM concentration. Control siRNA-SQ was prepared using the same protocol. The size of the nanoassemblies was determined by dynamic light scattering and their zeta potential by their electrophoretic mobility. Cryo-transmission electron microscopy was used to observe the morphology of these squalene-based nanoassemblies. Nanoassembly stability and drug release was tested in phosphate buffer (PBS) and in cell culture medium.

The detailed protocol for obtaining bioconjugates siRNA PMP22-SQ is described below.

(i) Bioconjugation of siRNAs

One nmole of the 5'-end modified sense strand DBCO-$C_6$ of the siRNA PMP22 (1 mg/mL in DNAse/RNAse-free water) was mixed with 50 nmoles of SQ-$N_3$ (1 mg/mL in DMSO) in a glass vial containing DMSO (286 µL) and acetone (65 µL). The solution was then incubated at room temperature for 12 h under stirring to obtain the bioconjugate siRNA PMP22-SQ. In the next day, excess acetone was removed under nitrogen flow for 30 min followed by lyophilization step.

Purification of the bioconjugate from the excess of unconjugated SQ was performed by RP-HPLC on a polymeric column as described below. The identity of the bioconjugates siRNA PMP22-SQ was confirmed by MALDI-TOF mass spectrometry. Purified products were lyophilized, and then solubilized into RNAse free water at the desired molar concentration at 10 µM. The same protocol was performed to obtain the siRNA Ct-SQ bioconjugate.

(ii) Purification of siRNAPMP22-SQ Bioconjugates Via HPLC

HPLC purification was performed on a thermoscientifc high-performance liquid chromatography system (UltiMAte3000) equipped with a photodiode array detector whose wavelength range between 190 and 800 nm, a pump, and a manual injector. The stationary phase consisted of a nonporous, alkylated polystyrene divinylbenzene column (Hamilton PRP-3 10 µm, 4.6×250 mm, PEEK, Ref: 79574) protected by pre-column (Hamilton). Thermofisher Chromeleon software was used for data acquisition with a flow rate of 1.2 mL/min and injection volumes of 100 µL. A gradient of mobile phases A and B was applied. Mobile phase A composed of: 0.2 M TEAA (5%), pH 7.0, with 5% acetonitrile, water 90% while mobile phase B consisted of 95% acetonitrile with 5% TEAA, 5% of water. The gradient applied for purification was as follow: 0-8 min linear gradient from 0% to 24% of phase B; 8-16 min linear gradient from 24% to 90% of phase B; 16-18 min linear gradient from 90% to 100% of phase B; 18-30 min 100% of phase B; 30-32 min linear gradient from 100% of phase B to 100% of phase A and 32-42 min re-equilibration with 100% phase A. Bioconjugate siRNA-SQ was purified by manual peak collection. Fractions were collected for 2 min, corresponding to a fraction volume of 2.4 mL, and then lyophilized. All lyophilized siRNA fractions were reconstituted in DEPC-treated water.

(iii) MALDI-TOF Mass Spectrometry

A MALDI-TOF/TOF UltrafleXtreme mass spectrometer (Bruker Daltonics, Bremen) was used for all experiments. Mass spectra were obtained in linear positive ion mode. The laser intensity was set just above the ion generation threshold to obtain peaks with the highest possible signal-to-noise (S/N) ratio without significant peak broadening. All data were processed using the FlexAnalysis software package (Bruker Daltonics).

(iv) Annealing of siRNA-SQ Bioconjugates to Antisense siRNA Strands

Annealing of both strands of siRNA PMP22 and siRNA Ct was performed after the bioconjugation of the sense strand to SQ according to the manufacturer protocol and the same as mentioned before for the generation of siRNA from single RNA strands. Precisely, equimolar amounts of both siPMP22C6-SQ bioconjugate and antisense siPMP22 were mixed with an annealing buffer [30 mM HEPES-KOH (pH 7.4), 2 mM Mg acetate, 100 mM K acetate] and incubated at 95° C. for 3 min then incubated for 45 min at room temperature before storing at −80° C. or precipitation directly. The same protocol was performed to obtain siRNA Ct-SQ bioconjugate.

(v) Preparation and Characterization of Nanoparticles siRNAPMP22-SQ

Nanoparticles (NPs) siRNAPMP22-SQ and siRNA Ct-SQ were prepared by nanoprecipitation in acetone: water (1:2). One phase was slowly added to the other, under stirring i.e. 10 nmole of siRNA-SQ were dissolved in 1 ml of DEPC treated water and added drop wisely over 500 ml of acetone under stirring. Then the two solution were kept under stirring for 5 min after which acetone was completely evaporated using nitrogen flux to obtain an aqueous suspension of pure siRNA-SQ nanoassemblies at 10 µM concentration.

The hydrodynamic diameter (nm) was measured by Dynamic Light Scattering (DLS) Malden Zeta Sizer NANO. Samples were analyzed at 10 µM concentration in $H_2O$. Three measures of 5 min for each per sample were performed and the average diameter±S.D. of three independent samples was calculated.

Cryogenic Transmission Electron Microscopy (cryo-TEM) was performed with the JEOL 2100 electron microscope at the Electronic Microscopy Platform (IBPS/Institut de Biologie Paris-Seine, Université P. et M. Curie, Paris, FRANCE). A drop of 4 µL of siRNA PMP22-SQ NPs (concentration of 2.2 mg/mL) was deposited on a carbon-coated copper grid. Excess of the liquid was removed with blotting filter paper, and the samples were quickly vitrified by plunging them into liquid ethane using a guillotine-like frame. The samples were then transferred to a cryo-sample holder. Observations were made at an acceleration voltage of 200 kV under a low electron dose. Analysis was performed with Image J software.

Effects of siRNA PMP22-SQ Nanoparticles in a Conditional CMT-1A Transgenic Mouse Model This study was first performed in vivo in a mouse model of CMT-1A established by Perea et al. (*Hum Mol Genet* 10, 1007-1018, 2001). In this model overexpression of PMP22 occurs specifically in Schwann cells of the peripheral nerves and causes demyelination responsible of CMT-1A disease.

The transgenic mice were purchased from TAAM CNRS after reviviscence of oocytes in two genetic backgrounds B6 and CBA. At 3 month of age molecular and behavioral studies were performed on JP18 B6 and CBA to study their gene expression of PMP22, motor and sensory functions respectively. This mouse model comprises one extra copy of the PMP22 gene. All the data were compared between CMT-1A mice in B6 or CBA backgrounds to WT mice. For the JP18 mouse model, the mouse pmp22 cDNA was introduced under control of the PhCMV*-1 promoter, therefore, mice overexpressed pmp22 throughout life.

This study was also performed on double transgenic mouse model (JP18/JY13). This model was generated by crossing JP18 and JY13 mice and comprises two extra copies of the PMP22 gene. In absence of tetracycline, pmp22 overexpression occurs throughout the mice lifespan. At ten days of age, mice were systematically genotyped as previously described by Robertson et al., by using specific primers for PMP22 and tTA sequences.

Impact of the Administration of an siRNA Against PMP22 on the Progression of CMT-1A Pathology JP18B6 mice were divided into 3 groups 5 mice each in addition to a wild type group as a comparison. One group was given a vehicle of 5% dextrose solution, the second was treated with siRNACTRL-SQ NPs and the third was treated with siRNAPMP22-SQ NPs. All the treatments were administered by sub ocular IV injection of a cumulative dose of 2.5 mg/Kg at an interval of 0.5 mg/kg per injection twice per week (5 treatments in total). At the end of the treatment, mice were sacrificed and the sciatic nerve was collected for further studies. All animal experiments were approved by the institutional Ethics Committee of Animal Experimentation (CEEA) and research council, registered in the French Ministry of Higher Education and Research (Ministère de l'Enseignement Supérieur et de la Recherche; MESR, APAFIS #I 0131-2016112916404689 vl 6) and carried out according to French laws and regulations under the conditions established by the European Community (Directive 2010/63/UE). Investigation has been conducted in accordance with the ethical standards and according to the Declaration of Helsinki. All efforts were made to minimize animal suffering: administration of treatments was performed under isoflurane anesthesia and animals were sacrificed by cervical dislocation. All animals were housed in sterilized laminar flow caging system. Food, water and bedding were sterilized before being placed in the cages. Food and water were given ad libitum.

The progression or regression of the pathology was monitored by the behavioral beam-walking test and grip test. These tests essentially examine the ability of the animal to remain upright and to walk on an elevated and relatively narrow beam and their muscular strength.

In another similar experiment to test siPMP22-SQ NPs on a more affected CMT1A mouse model, the double transgenic model (JP18/JY13) that harbour two extra copies of PMP22 genes were used. At 12 weeks of age JP18/JY13 mice were divided into three groups similar to the groups of JP18 mice. The same protocol of treatment was performed and 6 mice per group were used in addition to a Wild type B6 group. Behavioural tests were performed as mentioned for the JP18 B6 mice and sciatic nerves were collected after then.

To study the long lasting effect of siPMP22-SQ NPs JP18/JY13 B6 mice of 12 weeks age were used. Mice were again divided into three groups of 6 mice each: JP18/JY13 vehicle, JP18/JY13 siRNA Ct-SQ NPs and JP18/JY13 siPMP22-SQ NPs in addition to a wild type B6 group as a control. Two cycles of treatment were administered. The first cycle of treatment represents a cumulative dose of 2.5 mg/kg of siPMP22-SQ NPs and siRNA Ct-SQ NPs at an interval of 0.5 mg/Kg per injection twice per week. Then treatment were stopped for three weeks to check the relapse period and three mice per group were sacrificed at the end of the first treatment cycle and sciatic nerve were collected for further analysis. At week four, the new cycle of treatment was initiated for another cumulative dose of 2.5 mg/kg of siPMP22-SQ NPs and siRNA Ct-SQ NPs at an interval of 0.5 mg/Kg per injection twice per week. Behavioural tests were performed before treatment, at 1.5 mg/kg of first treatment cycle, at 2.5 mg/kg of first treatment cycle, two weeks after stopping the first cycle treatment, three weeks after stopping the first cycle treatment, 1.5 mg/kg of second treatment cycle and 2.5 mg/kg of second treatment cycle. Sciatic nerves were extracted at the end of the second cycle for further analysis.

Behavioral Tests

Beam Walking test: Mice were placed on a platform with a rod of 3 cm diameter, 70 cm length and around 30 cm above a flat surface. At one end of the rod was set a secure platform to house the animal. First, the mouse was allowed to adapt and then trained to cross the beam after which the time taken to traverse, the speed, the number of stops and the number of left or right hindaw faults/slips were recorded for analysis. The animals were recorded for three trials per session before starting the treatment and at the end of the experiment. The behavior task repeated three times per animal was recorded using a high definition digital camera.

Locotronic: The locotronic apparatus was used to test motor coordination when walking. The mice crossed a 75×5×20 cm flat ladder with bars (7 mm in diameter), which were set 2 cm apart. Infrared photocell sensors situated above and below the bars monitored paw errors. The locotronic apparatus is linked to a software that automatically record the time taken by the mouse to cross the path as well as the paws errors. The time and the errors were assessed in three trials, with 15 min rest between trials. The test was performed at the end of the treatment. Statistical analysis of obtained data was performed by calculating the mean of three trials per day over 3 days for each group. Data were presented as the mean±SD.

Grip strength test: Neuromuscular force was assessed by using the Grip strength test. This test was performed using a computerized grip strength meter. The apparatus consisted of a T-shaped metal bar and a rectangular metal bar connected to a force transducer. To measure force in the fore paws of the mice, each mouse was held gently by the base of the tail, allowing the animal to grasp the T shaped metal bar with its forepaws. As soon as the mice grasped the transducer metal bar with their forepaws, the mouse was gently pulled backwards by the tail until grip was lost. This step was repeated three times and the highest force was automatically recorded in grams (g) by the device. To measure the force on both limbs, each mouse was allowed to grasp the rectangular metal by the fore and hind limbs. After that it was gently pulled by its tail perpendicular to the axes of the apparatus until the mouse looses the grip. The highest force was recorded automatically by the device.

Hot Plate test: The sensitivity to heat was assessed using the Hind paw withdrawal test. The platform onto which animals were placed was set at 52° C. and the time to sense the heat and withdraw their paws was recorded for analysis.

Electrophysiological Study

The test was done with a standard EMG apparatus (Natus/EMG) in accordance with the guidelines of the American Association Of Neuromuscular And Electrodiagnostic Medicine. Anesthesia was performed by isoflurane inhalation where mice were place in an induction chamber containing 1.5-2% isoflurane in pure oxygen. During the whole procedure, anesthesia was maintained on the same level through a face mask. Mice were placed on their frontal side on a heating pad to maintain their body temperature between 34 and 36° C. For recording the compound muscle action potential, the stimulator needle electrode was inserted at the sciatic nerve notch level, the anode electrode was inserted in the upper base part of the tail while the receptor needle or the recording needle was inserted in the medial part of the gastrocnemius muscle. A supramaximal square wave pulse of 8 mA was delivered through the stimulator needle and recorded through the muscle as amplitude. For the measurement of sensory nerve conduction velocity multiple stimulation of the caudal nerve was delivered through the stimulator needles that were located at the ⅔ of the length of the tail with a distance of 2-2.5 cm from the receptor needles. The ground electrode was inserted half way between the stimulator and the receptor electrodes. The sensory nerve conduction velocity was calculated from the latency of the stimulus and the distance between the stimulator and receptor electrodes.

Biological Tests

The sciatic nerve histology of CMT-1A animals (treated or not with siRNA) was studied by electron microscopy where the number of myelinated or unmyelinated axons and the thickness of myelin sheaths is assessed by determining the g-ratio. Then the number of mitochondria per axon was calculated to assess the axonal suffering. RT-qPCR and Western blots experiments were performed to evaluate the effects of siRNA on PMP22 expression in the sciatic nerves of CMT-1A mice. PMP22 expression was normalized to control level (WT animals or CMT-1A mice treated with siRNA PMP22). The neuromuscular junction (NMJ) of CMT-1A mice treated or not with siRNA PMP22 is analyzed by immunohistochemistry. Muscle weakness in CMT-1A has been attributed to an axonopathy, resulting in muscle denervation and atrophy.

Neuromuscular junction loss is observed in CMT-1A. It is important to study the NMJ to determine the effectiveness of siRNA therapy. Using confocal and electron microscopy, a comprehensive study of the structure of the NJM (innervation, denervation, reinnervation . . . ) is performed.

Pharmacokinetics and Biodistribution Studies

Radiolabeled free or SQ-conjugated siRNA PMP22 (siRNA PMP22-SQ $^{32}$P NPs) is injected intravenously in transgenic mice bearing CMT-1A. Organs and blood are collected at different time points and concentration of free vs. siRNA PMP22-SQ NPs was determined counting the radioactivity by a g counter. Also, it is verified by "Radio-HPLC" analysis that the siRNA PMP22 is not degraded once accumulated within the desired tissue. Pharmacokinetic parameters are calculated (e.g. plasma half-life and clearance). Noteworthy, more than 50% of squalene is transported by LDL and HDL lipoproteins therefore; the possible interactions of siRNA PMP22-SQ NPs with blood constituents (i.e. LDL, HDL, VLDL, blood cells etc.) are evaluated as previously described by Sawle et al. (Journal of lipid research 43, 335-343, 2002).

Statistical Analysis

All data were presented as mean±standard deviation (SD). Non parametric Kruskal-Wallis analysis followed by Dunns tests or Anova followed by Bonferroni tests were used to compare multiple treatments using GraphPad Prism. $p<0.05$ was considered as a statistically significant level.

Results

Effects of siRNA PMP22 on PMP22 mRNA Expression in MSC-80 Cells

Figure 2:
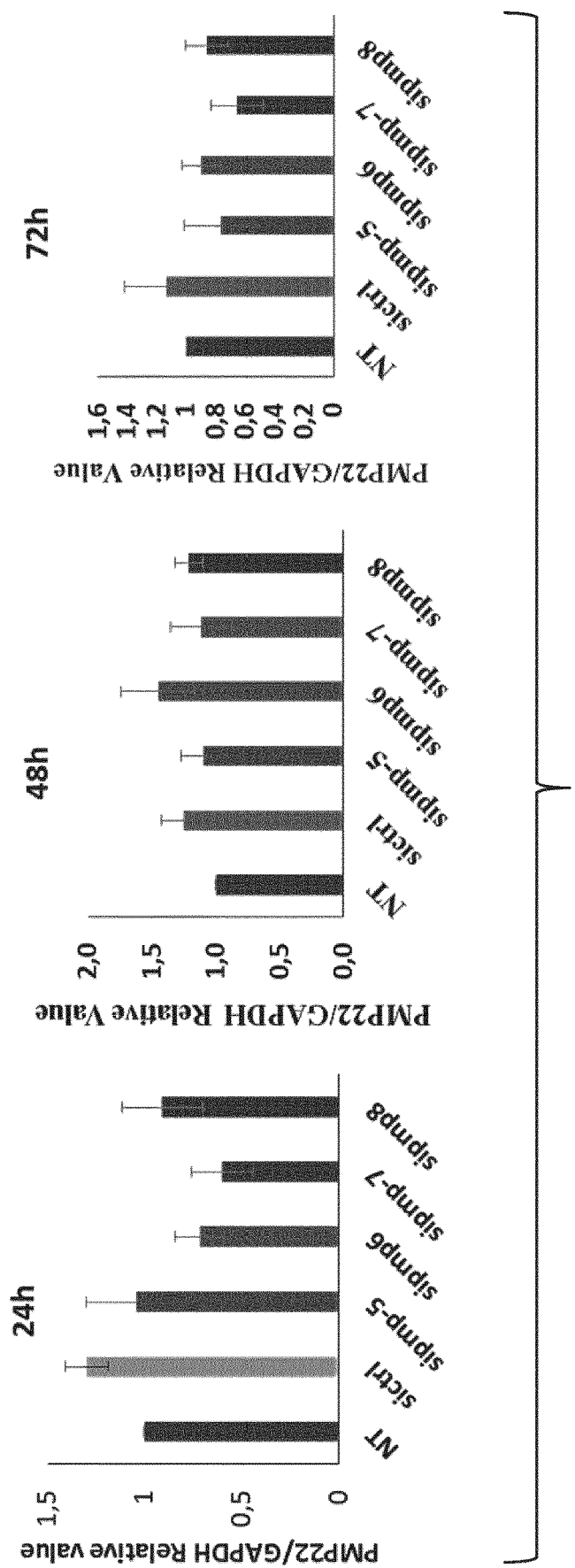
FIG. 2: Effect of siRNAs PMP22 on PMP22 protein level. Protein levels were assessed by Western blot on siRNAs 5, 6, 7 and 8. Quantification of relative PMP22 protein expression over GAPDH is represented by bars.

First the effect of siRNAs PMP22 (1 to 8) on mRNA PMP22 expression was studied. It was compared to the effect on siRNA control, a scramble sequence to non-treated cells. By using Kruskal-Wallis followed by Dunns tests, it was found that all the siRNAs down regulate significantly PMP22 expression for 24 h and 48 h, except for siPMP6. After 72 h of transfection, siPMP4, 5, 7 and 8 were able to decrease the PMP22 gene expression by 50% when compared to the control (see FIG. 1). In addition after 72 hrs of transfection it was found that siPMP7 was able to not only decrease the gene expression of PMP22 but also decreased its protein expression (see FIG. 2).

Effect of Different Concentrations of siPMP22 on mRNA PMP22 and P0 and on Cell Viability.

Figure 3:
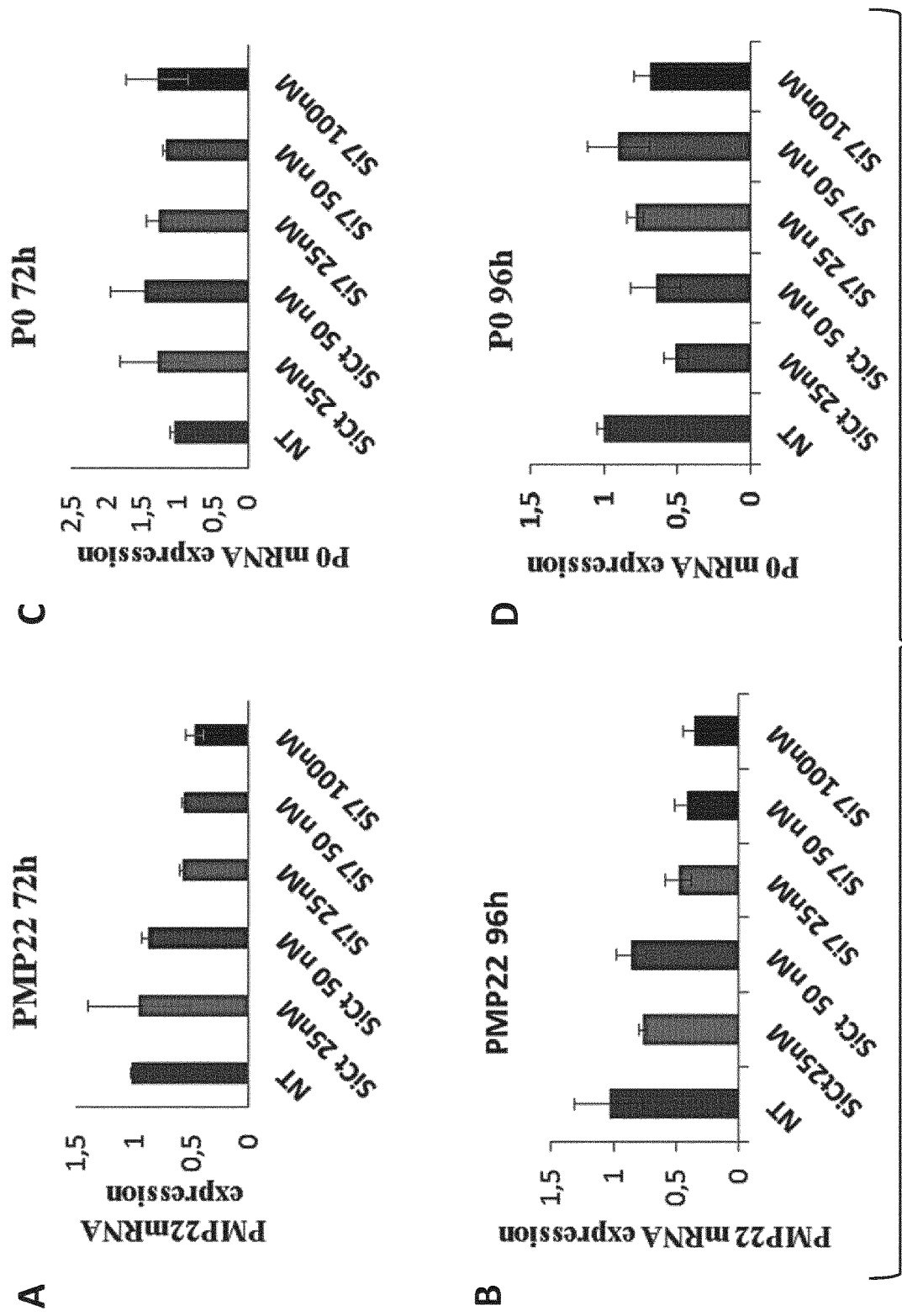
FIG. 3: Effect of different concentrations of siRNA PMP22 on PMP22 and P0 mRNA expression. siRNA control (siCt) was transfected for 72 h and 96 h at 25 nM and 50 nM, as well as siPMP22 #7 (si7) at 25 nM, 50 nm and 100 nM in MSC-80 cells. PMP22 and P0 expressions was assessed by real-time PCR and normalized on GAPDH expression. The 50 nM concentration was found to decrease PMP22 mRNA expression of 50% and had a long lasting effect (until 96 h) without affecting P0 mRNA expression.
Figure 4:
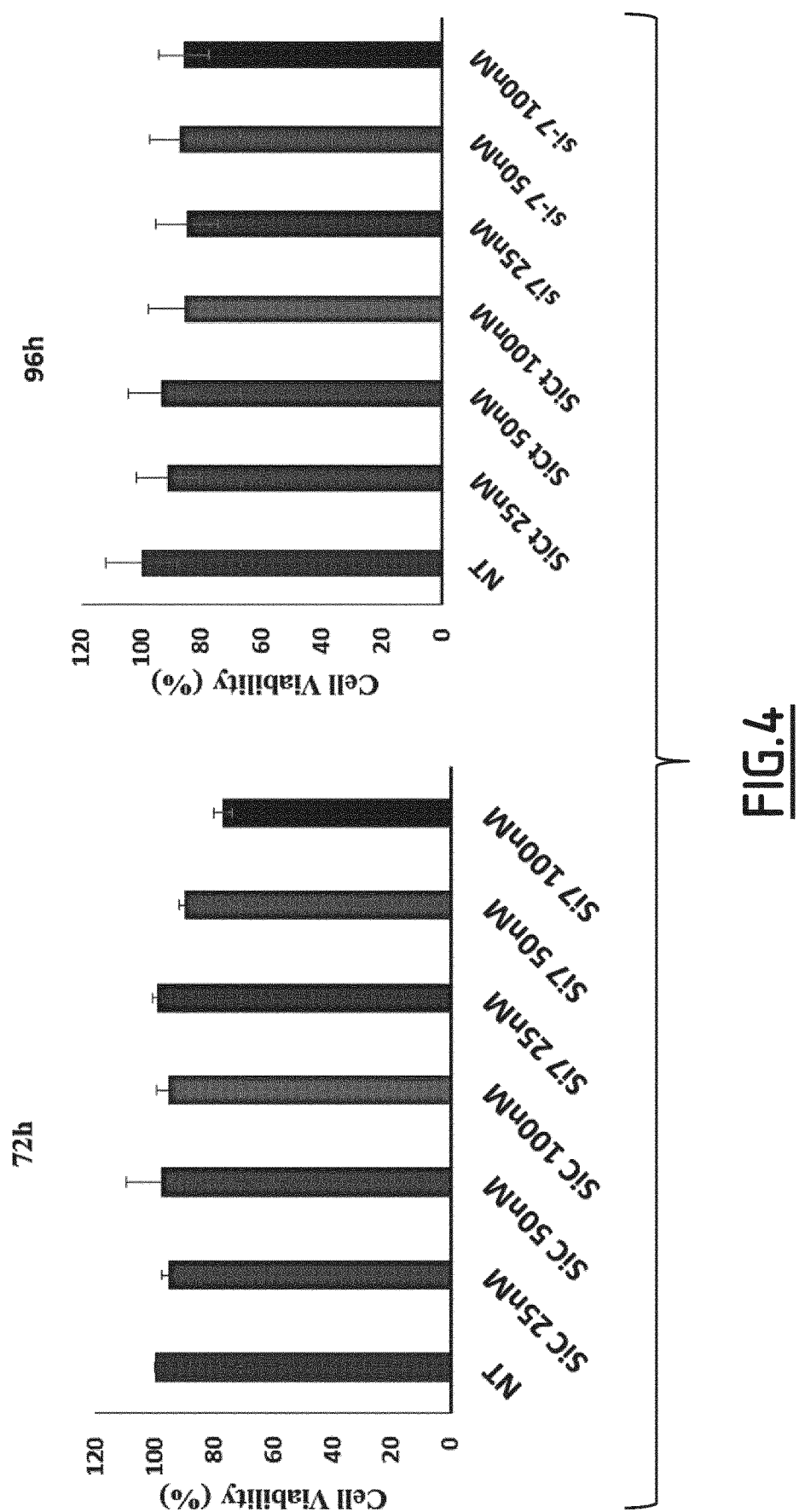
FIG. 4: Effect of different concentrations of siRNA PMP22 on cell viability. Cell viability was assessed by using MTT assay after 72 h and 96 h transfection of siRNA control and siRNA PMP22 #7 at the same concentrations as in FIG. 3. The 50 nM concentration has no significant effect on MSC-80 cell viability.

After that was studied the effect of different concentrations (25 nM, 50 nM and 100 nM) of siPMP7 on the gene expression of PMP22 and P0 by transfection of MSC80 cells for 72 and 96 h, in order to determine the optimal concentration capable of normalizing PMP22 expression without affecting P0 expression, a protein involved with PMP22 in myelin compaction and cell viability. Our results show that the optimal concentration is 50 nM. siPMP7 (50 nM) decreased the gene expression of PMP22 by 50% for 72 and 96 h respectively while it didn't affect P0 gene expression (see FIG. 3). Also cell viability test by MTT assay has shown that siPMP7 50 nM has no significant effect on MSC80 viability (see FIG. 4). The siRNA control (siCt) does not modify the expression of the two genes studied and cell viability.

siPMP7, thereafter named siPMP22, was the best candidate to continue the study on since it has the ability to decrease PMP22 levels by 50%, it didn't affect P0 levels and had no effect on the viability of cells in vitro.

The sequence of the siRNA PMP22 is:

```
Sense strand:
                                    (SEQ ID NO: 7)
5'-AUACCAACUGUGUGGACUA-3'

Antisense strand:
                                    (SE ID NO: 18)
5'-UAGUCCACACAGUUGGUAU-3'
```

Figure 12:
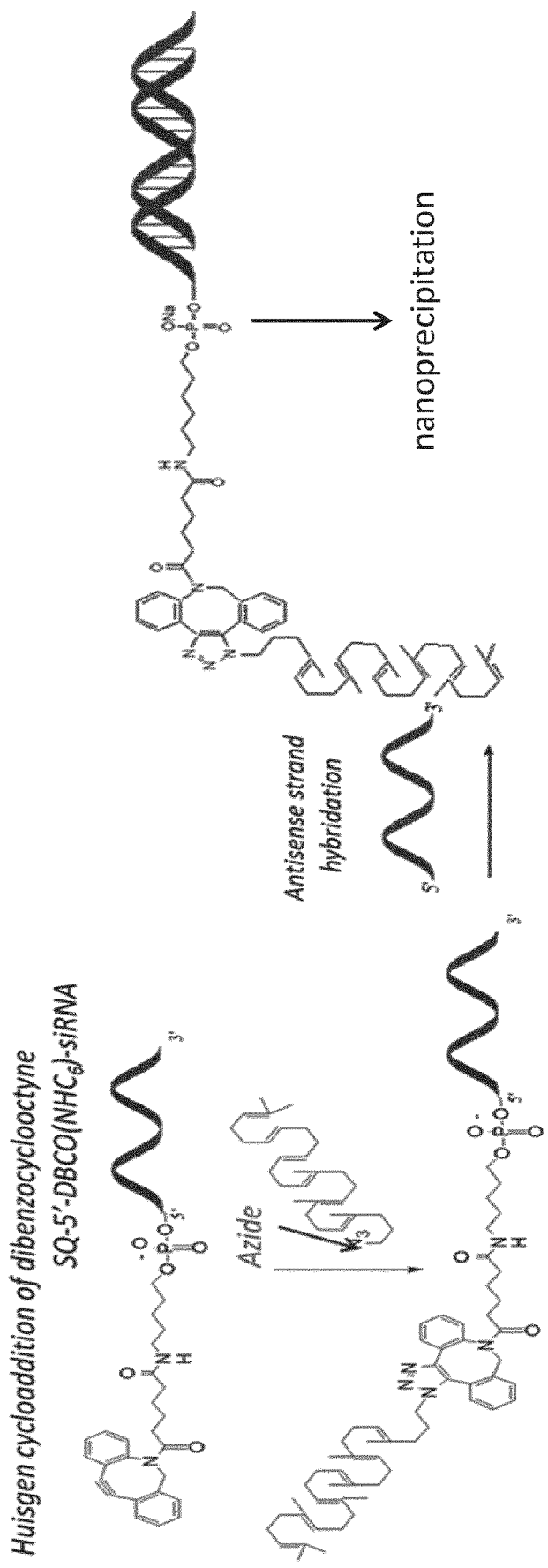
FIG. 12: Schematic representation of the synthesis of conjugated siRNA-squalene by strain-promoted Huisgen cycloaddition of dibenzocyclooctyne SQ-5'DBCO(NHC$_6$)-siRNA. For simplicity, only one regioisomeric triazole is shown. A. Synthesis of siRNA PMP22-SQ bioconjugate: Molar ratio siRNA:SQ 1:50; Solvents: DMSO, Acetone, water; Temperature: Room temperature; Incubation time: overnight, under stirring; B. Elimination of Acetone: Under nitrogen flow. C. Purification by HPLC. D. Elimination of organic solvents by lyophilisation; E. Bioconjugate annealing with AS (antisense) strand; F. Bioconjugate solubilisation in water:Acetone (2:1).

Coupling of siRNAPMP22 and siRNA CTRL to Squalene (SQ) and Characterization of siRNA PMP22-SQ Nanoparticles The bioconjugate siRNA PMP22-SQ and siRNA CTRL was obtained by Cu-free click chemistry with a yield of more than 90% thank to the optimized condition of the reaction detailed in FIG. 12. For siRNA PMP22-SQ, the collected bi-product identified by HPLC and analysed by MALDI-TOF MS showed that the bioconjugate have the expected molecular weight of 7628 (data not shown). The resulting bioconjugate was annealed with the anti-sense strand and nanoprecipitated in RNAse free water. The solution gave a Tyndall effect suggesting the formation of nanoparticles. Dynamic light scattering analysis (DLS) and the cryoTEM images showed the formation of stable nanoparticles for 30 days of about 180 nm with a good polydispersty Index (between 0.14 and 0.2) reflecting a homogenous solution suitable for an IV injection (see Table 4). For the siRNA CTRL the molecular weight identified by MALDI-TOF MS after bioconjugation and collection of the product was 7621 Dalton. DLS measurements showed that the size of siRNA CTRL-SQ NPs are stable over the period of one month (size: 255±2 at Day 0 and 238±4 at Day 30) and polydispersity index (0.15±0.02 and 0.1±0.01 respectively at Days 0 and 30).

TABLE 4

DLS measurements: size and polydispersity of siRNA PMP22-SQ NPs are stable over the period of one month

| siRNA PMP22-SQ NPs | Size(nm) | Polydispersity |
|---|---|---|
| Day 0 | 180.5 ± 4.01 | 0.2 ± 0.02 |
| Day 7 | 173.3 ± 1.75 | 0.16 ± 0.01 |
| Day 14 | 171.0 ± 1.96 | 0.16 ± 0.02 |
| Day 21 | 171.1 ± 6.59 | 0.16 ± 0.01 |
| Day 30 | 171.0 ± 3.24 | 0.14 ± 0.01 |

Figure 5:
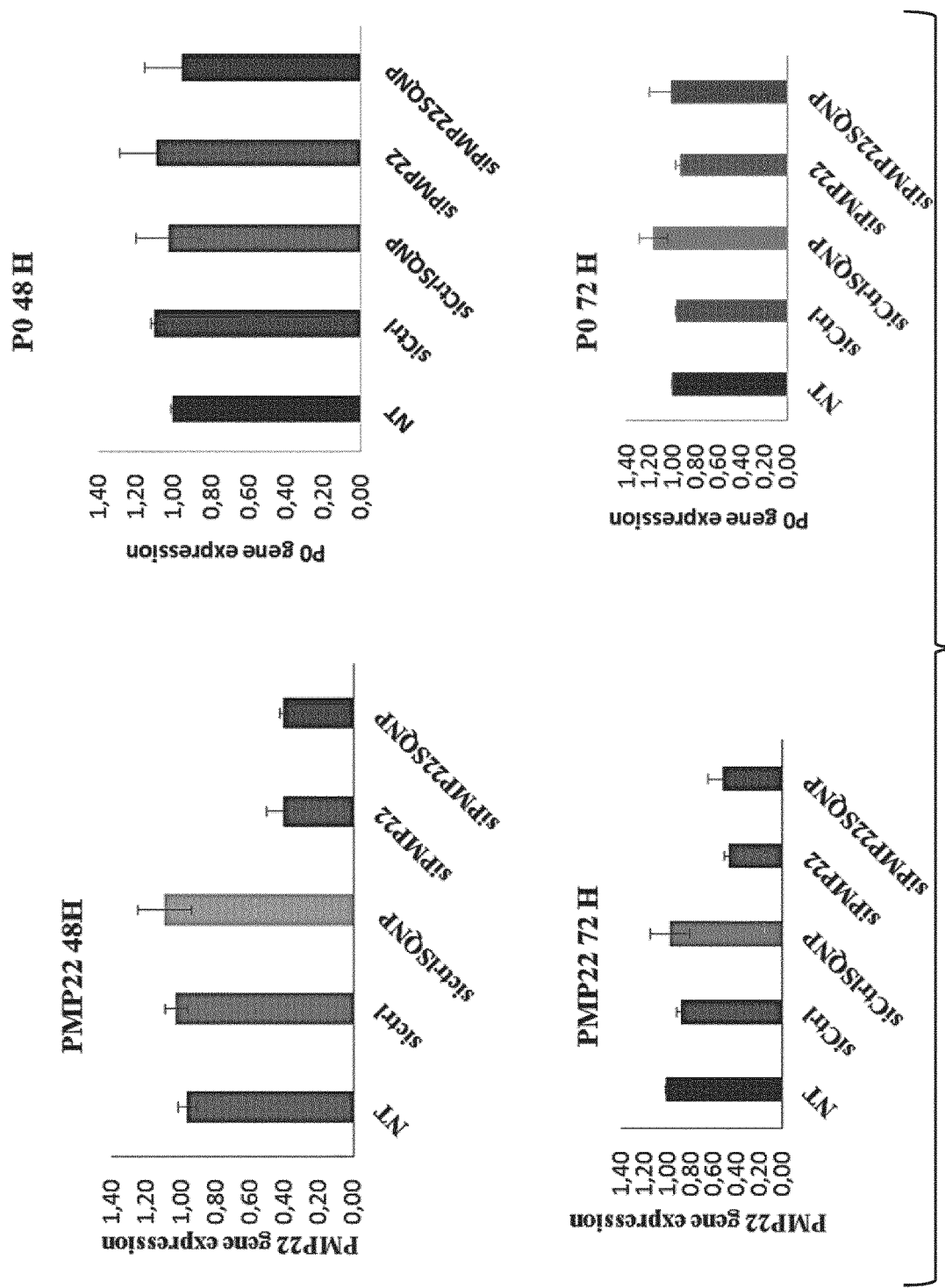
FIGS. 5 and 6: Efficacy in vitro of nanoparticles siRNAPMP22-SQ and effects on cell viability. MSC-80 cells were transfected by lipofectamine iMAX® for 48 h and 72 h by unvectorized siRNACtrl (siCtrl), vectorized with squalene (siCtrlSQNP), unvectorized siPMP22 (siPMP22) or vectorized with squalene (siPMP22-SQ NPs). After 48 h and 72 h cells were harvested, then mRNA were extracted to be analyzed for PMP22 and P0 genes expression (FIG. 5) and for cell viability (FIG. 6). The nanoformulated PMP22-SQ inhibited PMP22 products similarly to the unvectorized siRNA PMP22 overtime without affecting P0 expression and cell viability.
Figure 6:
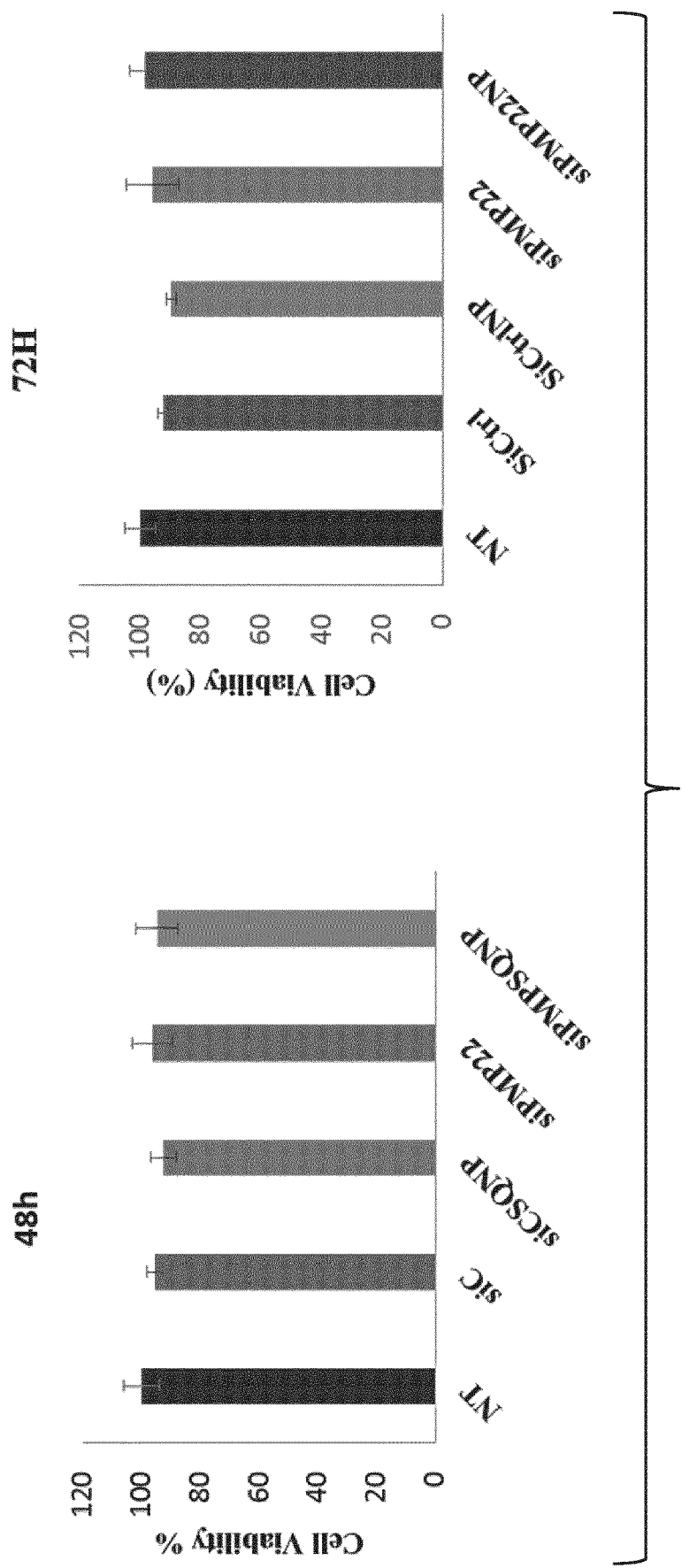

Then these nanoparticles siRNA PMP22-SQ and siRNA CTRL were tested in vitro for their efficiencies and effects on cell viability overtime (48 h and 72 h). Previously, we showed that the squalene based siRNA nanoparticles were not able to enter spontaneously into the cells without any cationic compound. Thus, SQ based siRNA PMP22 nanoparticles as well as the unvectorized siRNA PMP22 were transfected into MSC-80 cells by using lipofectamine iMAX®. After 48 and 72 hours, vectorized siRNA PMP22 were able to inhibit mRNA PMP22 similarly to the free siRNA PMP22 (see FIG. 5) without affecting cell viability (see FIG. 6). Moreover, siRNA Control nanoformulated or unvectorized did not affect PMP22 mRNA levels or cell viability when cells were transfected (see FIGS. 5 and 6).

Taken together, this part of the study showed that:
 i) squalenoylation of siRNA PMP22 gave a yield of ~100% after bioconjugation to SQ and ~85% yield after HPLC purification;
 ii) the resulted NPs are reproducible and stable over 1 month; and
 iii) the NPs were efficient in vitro: when transfected with lipofectamine, they inhibited PMP22 similarly to naked siRNA PMP22 and had no effect on cell viability.

In Vivo Experiments: PMP22 Gene Expression and Behavioral Tests on B6 and CBA Wild-Type and Transgenic PMP22 Mice First it was tested the expression of PMP22 on sciatic nerve by comparing the transgenic PMP22 mice in B6 and CBA backgrounds to their corresponding wild-type mice. For both PMP22 mice in B6 and CBA backgrounds, we found an increase of PMP22 mRNA expression compared to the wild-type. The P0 expression was found at the same level in both strands (see FIGS. 7A and 8 and FIGS. 8 A and 8).

Figure 7:
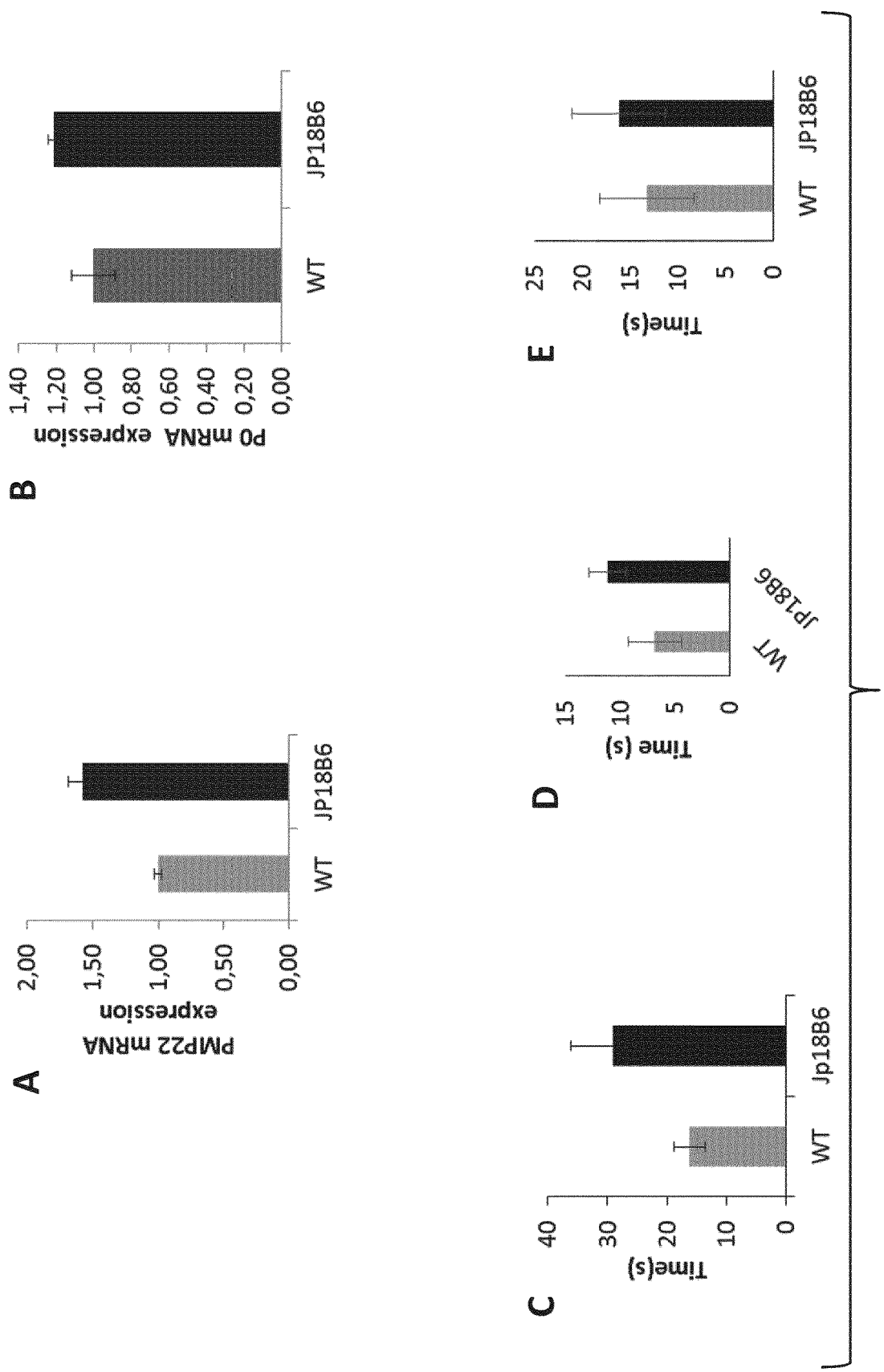
FIG. 7: PMP22 gene expression (A, B) and behavioral tests (C, D, E) on B6 wild-type and transgenic PMP22 mice (n=5). PMP22 (A) and P0 (B) mRNA expression assessed in the sciatic nerve of transgenic mice JP18 on B6 backgrounds to their corresponding wild-type mice. Behavioral tests performed on mice: beam walking test (C), locotronic (D) and paw withdrawal test (E).

Fine motor coordination and balance were assessed by the beam walking and locotronic assays. The goal of these tests is for the mouse to stay upright and walk across an elevated narrow beam to a safe platform. Interestingly, beam walking and locotronic assays showed an increase in time and number of fault for both PMP22 mice in B6 and CBA backgrounds compared to the wild type suggesting the development of CMT-1A disease. In fact, as seen in FIG. 7 C, D and in FIG. 8 C, a significant decrease in speed on the beam is observed in CMT-1A mice. Indeed, CMT-1A mice walk the distance twice slower than the control mice and the number of foot slips (faults) of CMT-1A animals is increased. The Paw withdrawal test that detect a noxious stimulus such as the feeling of pain, caused by stimulation of nociceptors (sensory neurons) was found to be identical for transgenic and wild-type mice suggesting that the sensory neurons of these transgenic mice are not affected. Therefore, the model used in our study is representative of CMT-1A pathology which is characterized by: i) an increase less than 2-fold of PMP22 expression due to 1.5 Mb duplication on chromosome 17p11.2, ii) decrease of motor neurons activity and iii) sensory neurons were not affected. Peripheral nerve injury tends to induce defects, which can cause the rodent to slip to one side.

Figure 8:
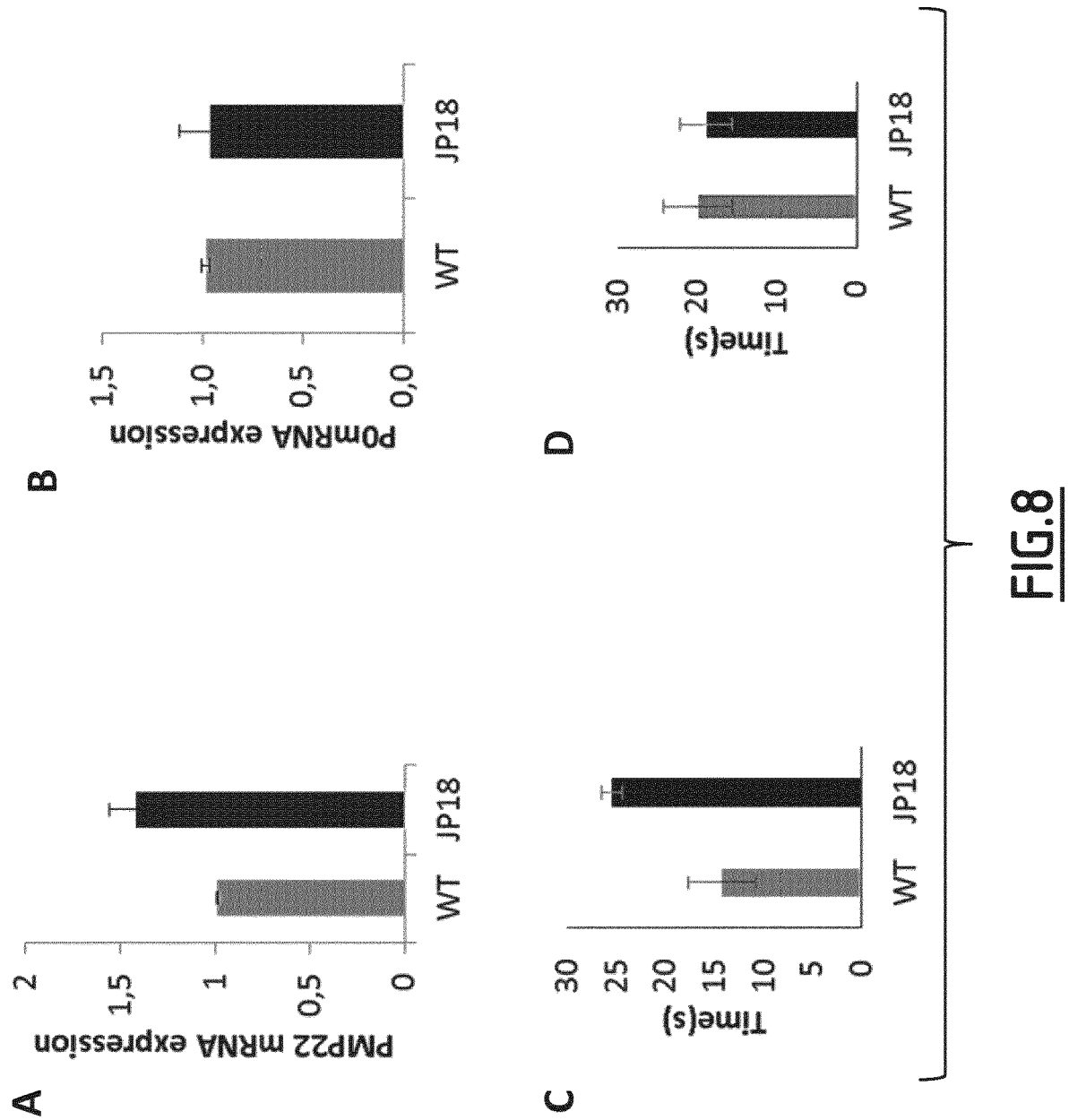
FIG. 8: PMP22 gene expression (A and B) and behavioral tests (C, D) on CBA wild-type and transgenic PMP22 mice (n=3). PMP22 (A) and P0 (B) mRNA expression assessed in the sciatic nerve of transgenic mice JP18 on CBA backgrounds to their corresponding wild-type mice. Behavioral tests performed on mice: locotronic (C) and paw withdrawal test (D).
Figure 9:
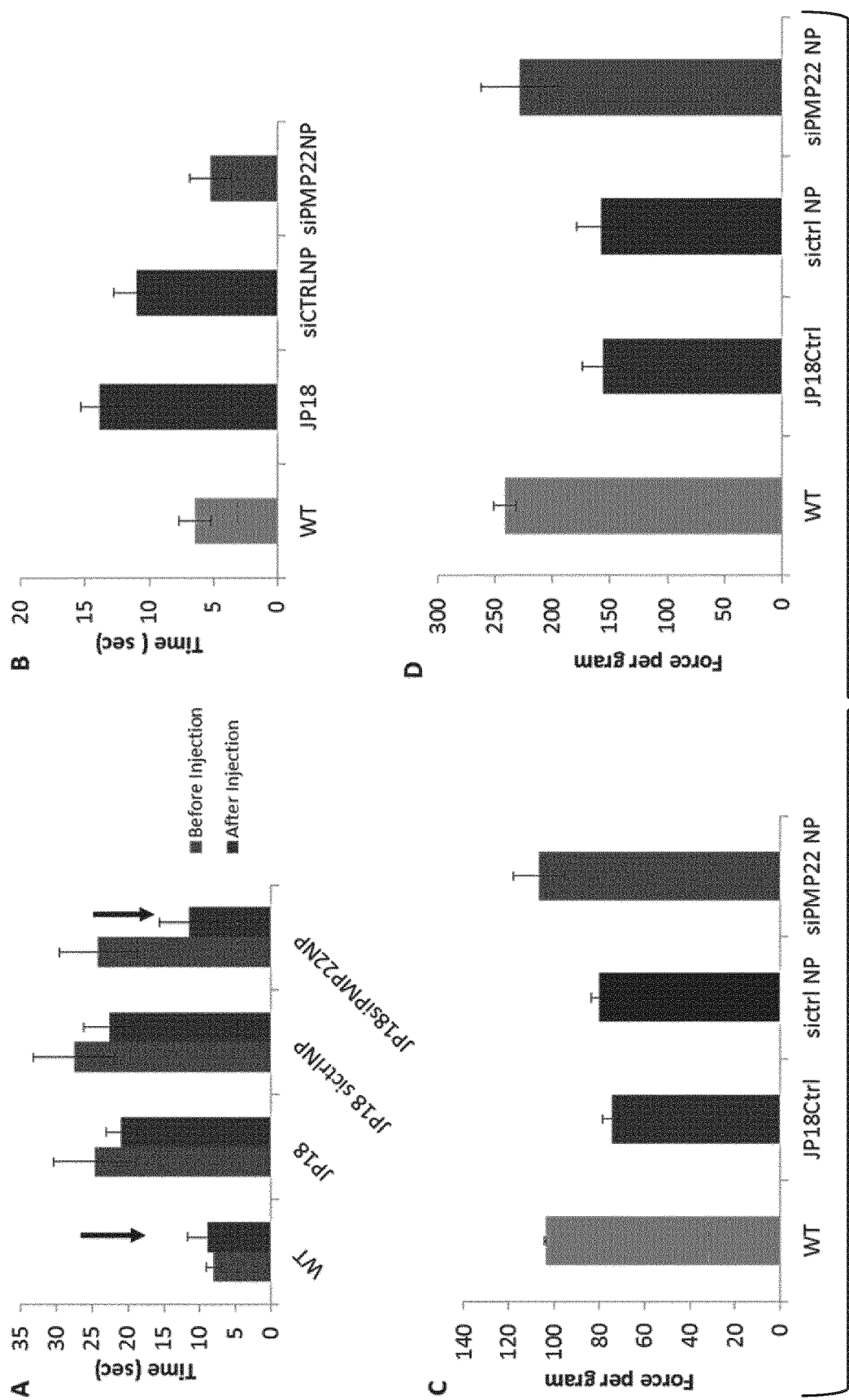
FIG. 9: Effects of nanoparticles PMP22-SQ on the behavior of JP18 B6 background (n=5/group). Mice were treated with vehicle (5% dextrose, nanoparticles siRNA control, nanoparticles siRNA PMP22). Then beam walking (A) and Locotronic (B) test in addition to grip strength test (strength forelimbs (C) and strength forelimbs and hindlimbs (D) were performed.
Figure 10:
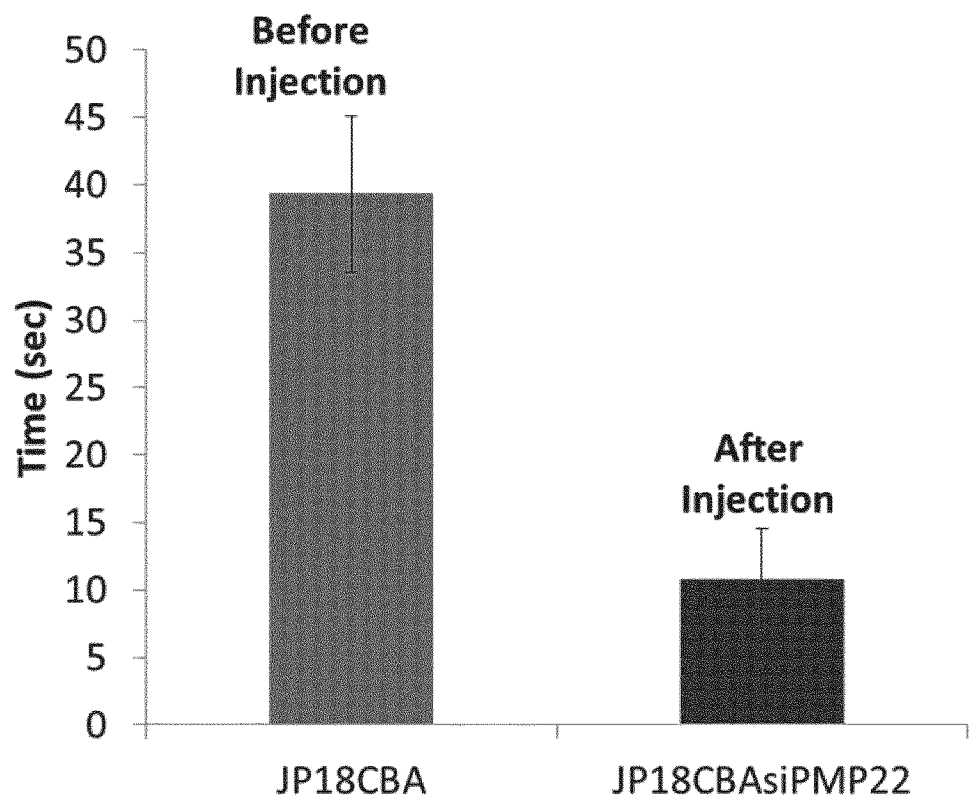
FIG. 10: Effects of nanoparticles PMP22-SQ on the behavior of mice on CBA background (n=3). Beam walking test was performed on mice before and after treatment with nanoparticles siRNA PMP22.
Figure 11:
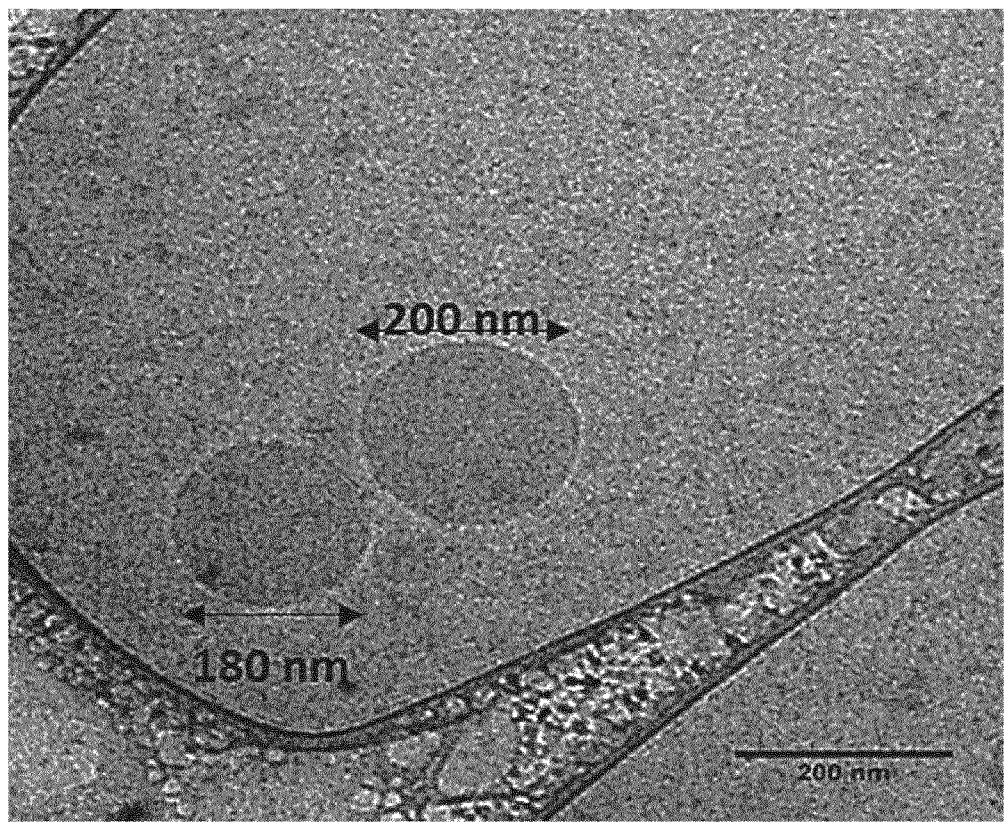
FIG. 11: Characterization of siRNA PMP22-SQ bioconjugate. The collected product was characterized by MALDI-TOF MS with a molecular weight of 7628 (data not shown), then after annealing with the antisense strand, the resulting nanoparticles were studied for their size by DLS (see Table 4 below) and for their form by Cryo-TEM (Cryogenic Electron Microscopy): the image shows that siRNA PMP22-SQ NPs have the same size obtained by DLS.

Effects of Nanoparticles PMP22-SQ on the Behavior of JP18 B6 and CBA Backgrounds Very interestingly, beam walking test done on JP18 on B6 background showed that the time spent by mice treated by the nanoparticles siRNA PMP22-SQ to cross the road is comparable to that of the untreated wild type mice (see FIG. 8 C; D). The mice treated with the vehicle (5% dextrose) or with the nanoparticles siRNA control-SQ did not show a difference in the time. Preliminary results on CBA mice showed the same result for the group treated with the nanoparticles siRNA PMP22-SQ (see FIG. 10).

Taking together, these results show that the nanoparticles siRNAPMP22-SQ can restore the motor activity of CMT-1A transgenic mice.

Figure 13:
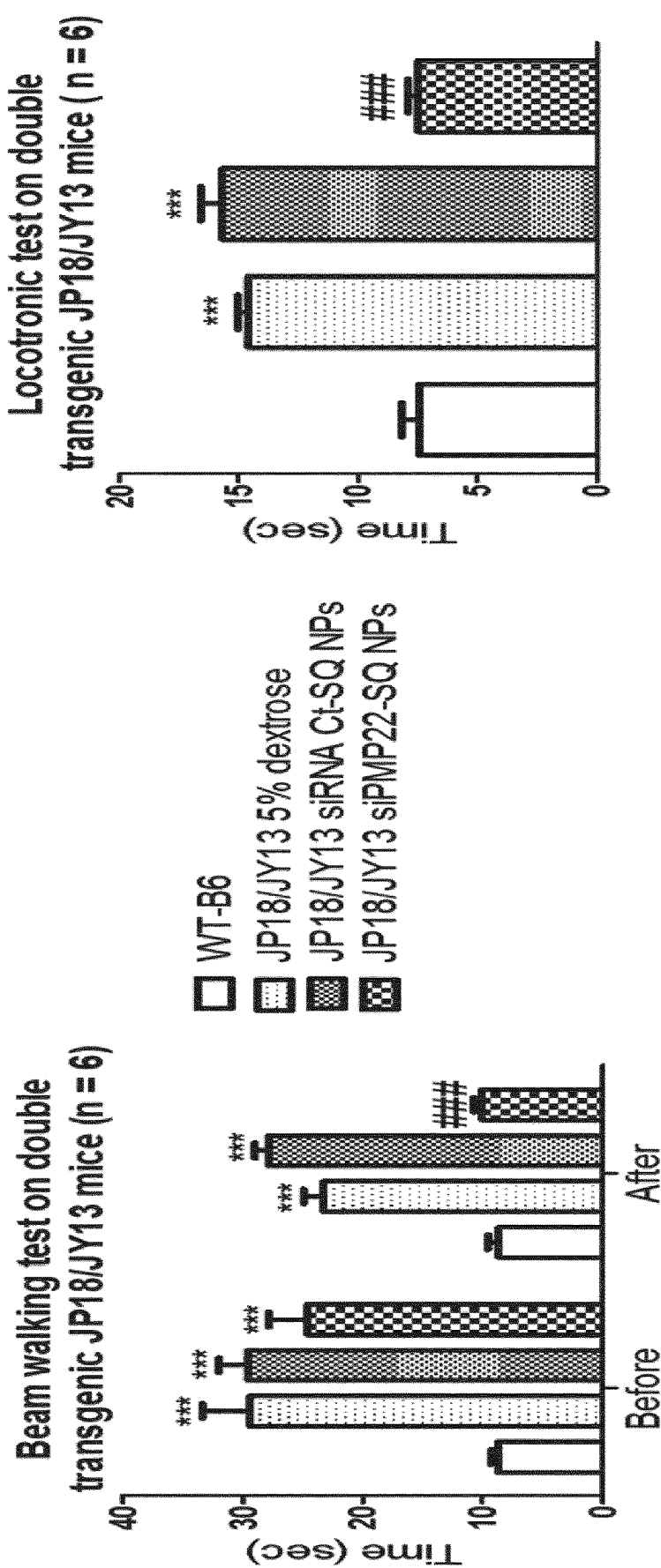
FIG. 13: Behavioral test analysis on double transgenic JP18/JY13 B6 CMT1A mice. Double transgenic mice of 12 weeks age were divided to on three groups (n=6 each). They received the following treatment: 5% dextrose, siRNA Ct-SQ NPs and siPMP22-SQ NPs, respectively. The wild type B6 group was used as a control. Beam walking test was performed before starting treatment and after treatment. The time taken by each mouse was recorded over three passages (mean±SD). JP18/JY13 siPMP22-SQ NPs group showed normalized time after treatment when compared to the WT-B6 group and were significantly faster than the groups receiving 5% dextrose and siRNA ct-SQ NPs. Locotronic test was performed after the end of the treatment and it showed significant results as the beam walking test. Three passages were recorded and the data shown is the average of 9 independent mice (mean±SD). (*) represent the significance between WT-B6 and other groups. (#) represent significance between siRNA Ct NPs group and other groups. ***, ###: $p<0.001$ (Anova followed by Bonferroni tests).
Figure 14:
FIG. 14: Grip strength test analysis on double transgenic CMT1A mice. Grip strength test was performed at the end of treatment on both the forelimbs alone and the total limbs. JP18/JY13 mice receiving siPMP22-SQ NPs group showed significant improvement in their muscular strength compared to the untreated mice (double transgenic 5% dextrose) and JP18/JY13 siRNA Ct-SQ NPs groups. Their strength became comparable to the muscular strength that of the WT-B6 group. (*) represents the significance between WT-B6 and other groups. (#) represent the significance between JP18/JY13 5% dextrose and JP18/JY13 siPMP22-SQ NPs. ***, ###: $p<0.001$ (Anova followed by Bonferroni tests).

The siRNA PMP22-SQ Nanoparticles Restore Motor Activity in Single and Double Transgenic Mice The locomotor activity of mice was tested by two complementary tests: the beam walking and the locotronic tests before and after the end of treatment. Also, the grip force was studied under the same conditions. We found that both JP18 (single transgenic) and JP18/JY13 (double transgenic) mice treated with siRNA PMP22-SQ nanoparticles have similar locomotion performance to wild type mice and significantly better than untreated mice (dextrose 5%) and treated with Ct-SQ nanoparticles (FIGS. 13 and 14).

Figure 15:
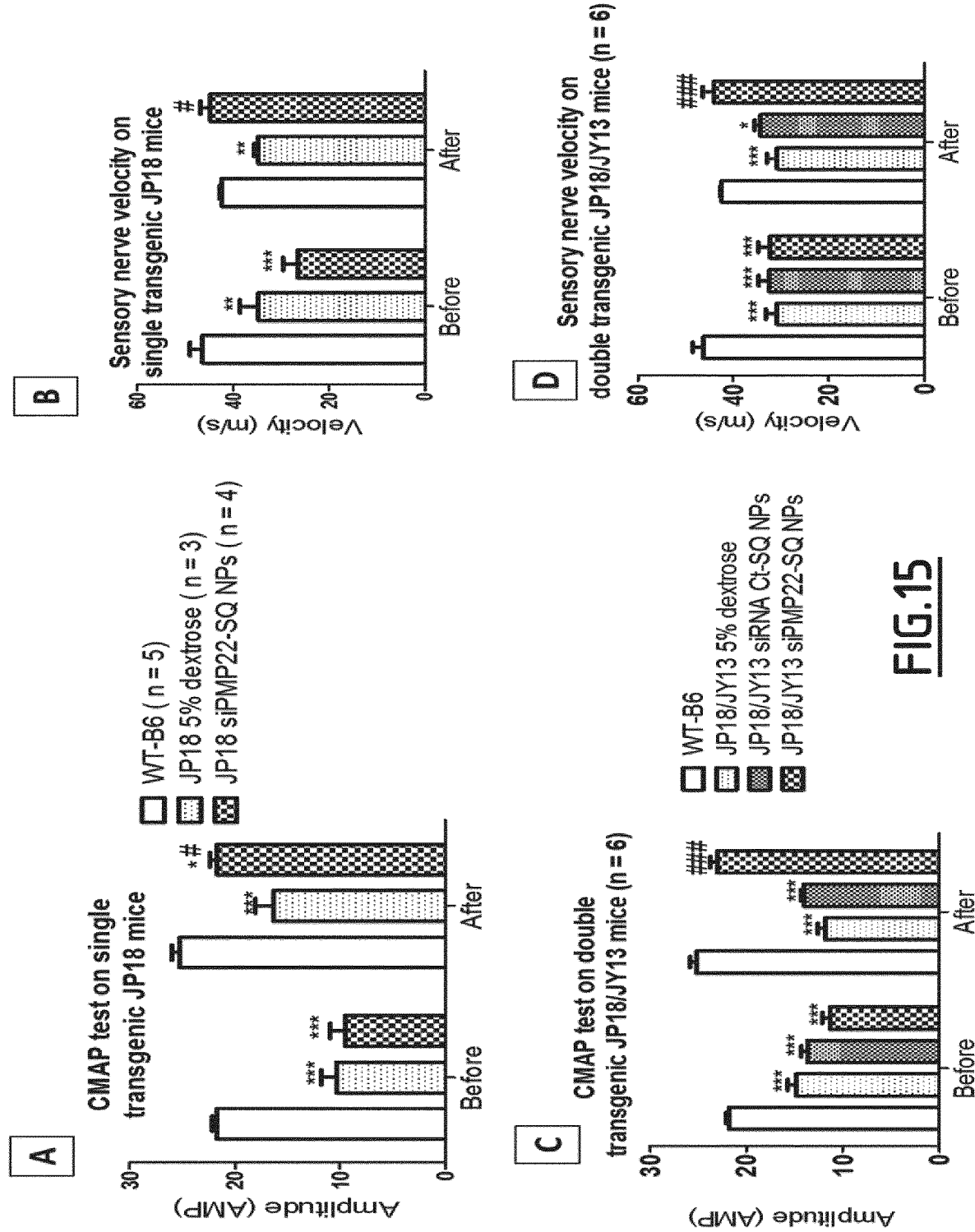
FIG. 15: Electrophysiological analysis on single transgenic JP18 (A and B) and double transgenic mice (C and D) JP18/JY13 CMT1A mice: Compound Muscle Action potential (A and C) and sensory nerve velocity (B and D). Data represent mean±SD. (*) represent the significance between WT-B6 and other groups. (#) represent the significance between JP18 or JP18/JY13 5% dextrose and JP 18 or JP18/JY13 siPMP22-SQ NPs. *#: $p<0.05$; : $p<0.01$, *, ###: $p<0.001$ (Anova followed by Bonferroni tests).

Electrophysiology Results siPMP22-SQ NPs restore Compound Muscle Action potential (CMAP) (see FIGS. 15 A and C) and sensory nerve velocity (see FIGS. 15 B and D) three weeks after treatment in both simple and double transgenic mice.

Figure 16:
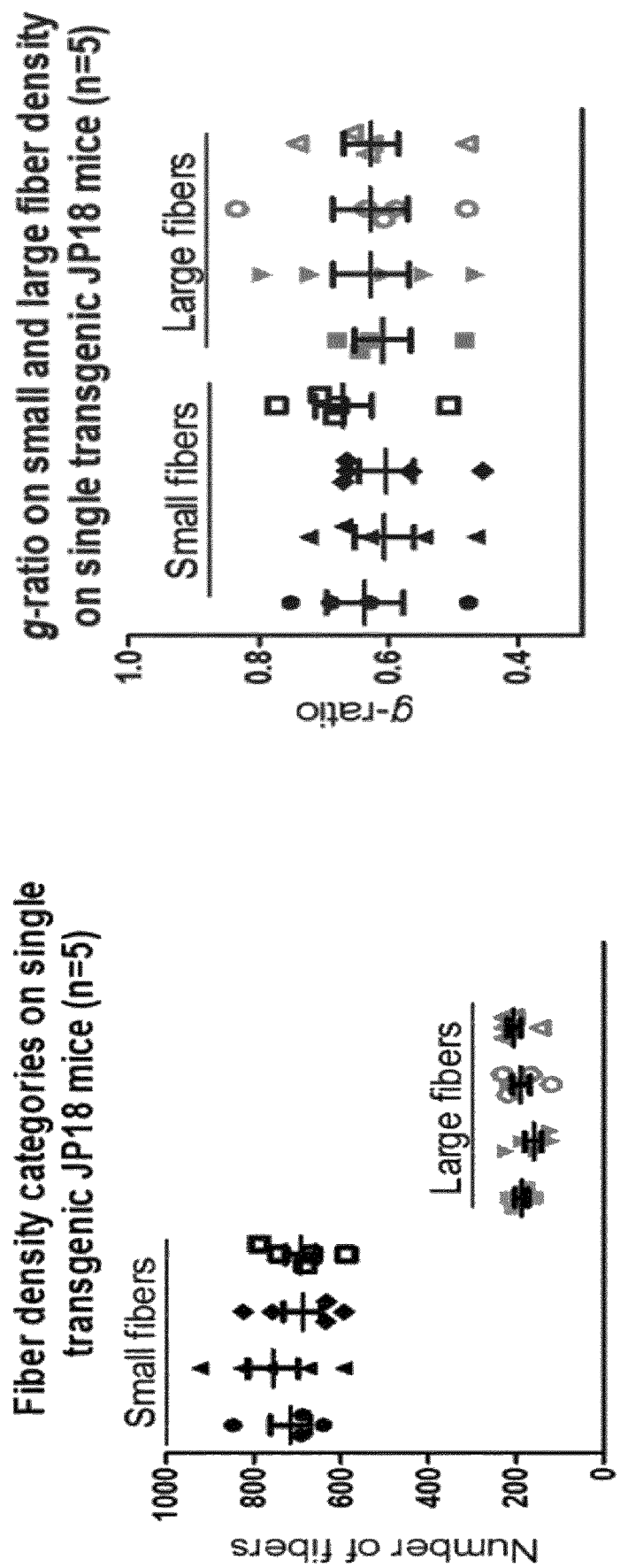
FIG. 16: Fiber density and g-ratio analysis on small and large fiber of toluidine stained semi thin sections on sciatic nerves of single transgenic JP18 CMT1A mice. No significant effect on myelination was detected between the different groups analyzed.
Figure 17:
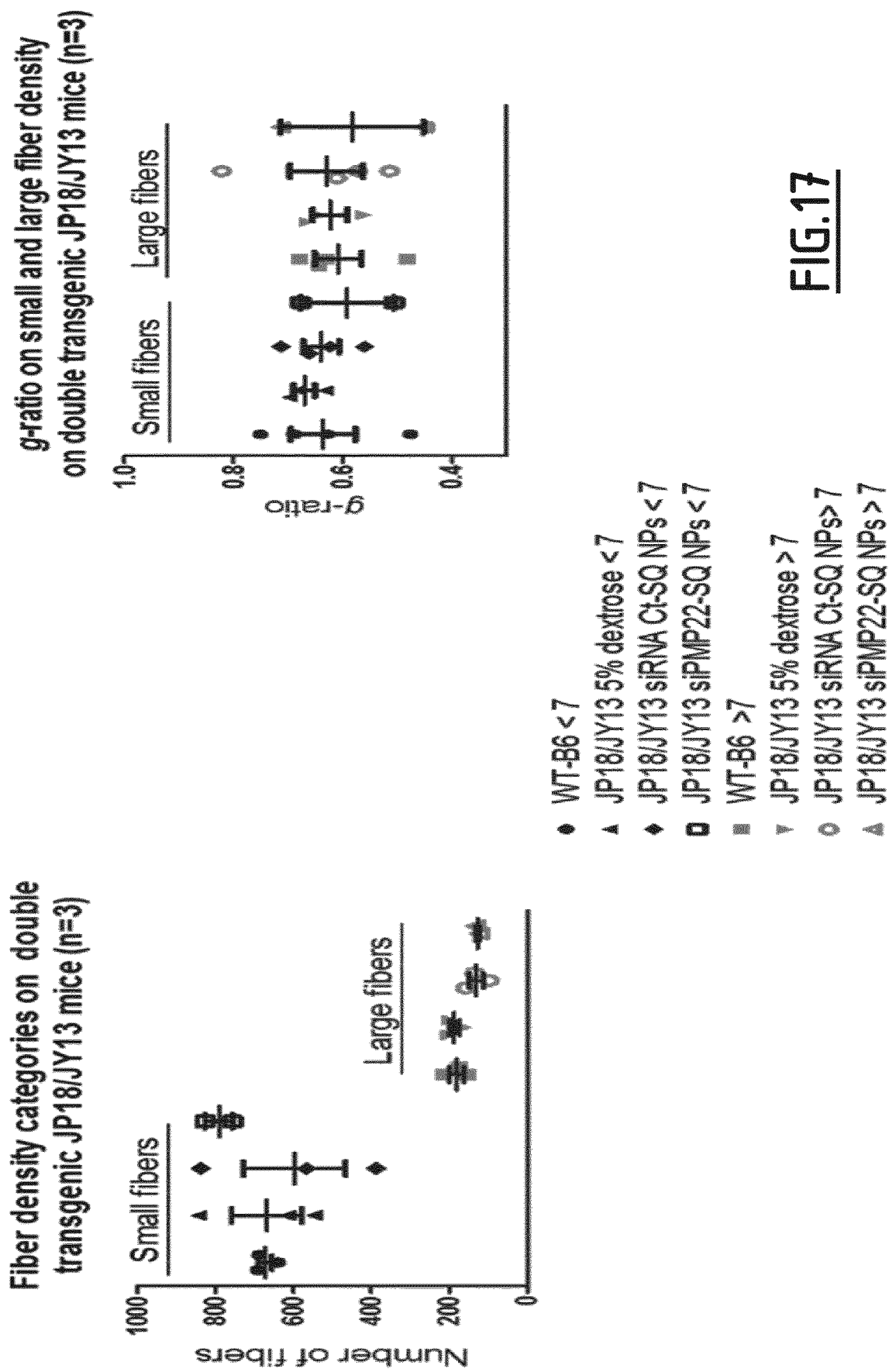
FIG. 17: Fiber density and g-ratio analysis on small and large fiber of toluidine stained semi thin sections on sciatic nerves of double transgenic JP18/JY13 B6 CMT1A mice. No significant effect on myelination was detected between the different groups analyzed.

Myelination and Axonal Regeneration siPMP22-SQ NPs did not modify the g-ratio in both simple and double transgenic mice (See FIGS. 16 and 17).

TEM micrographs of ultrathin section of sciatic nerves showed regulation of myelin sheath in simple and double transgenic mice treated with siPMP22-SQ NPs (data not shown). It was also shown that the nanoparticles were localized in the cytoplasm of Schwann cells and they can enter the nerve via the Ranvier nodes (data not shown).

Figure 18:
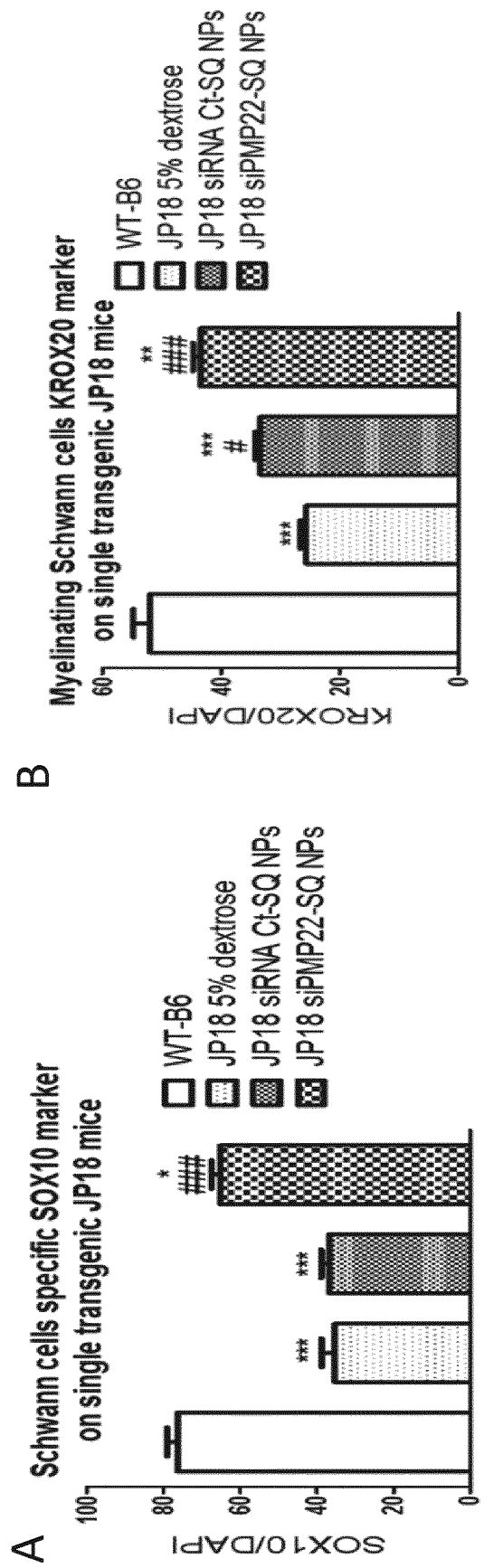
FIG. 18: Quantification analysis of the levels of transcriptional factor SOX 10 (A) and KROX20 (B) on single transgenic JP18 mice.
A. Data represents mean±SD and each group consists of three different mice. * represents the significance between WT-B6 group and the other groups and # represent significance between JP18 5% dextrose and JP18siPMP22-SQ NPs. *: $p<0.05$; ***: $p<0.001$, ###: $p<0.001$ (Anova followed by Bonferroni tests).
B. Data represents mean±SD and each group consists of three different mice. * represents the significance between WT-B6 group and the other groups and # represent significance between JP18 5% dextrose and JP18siPMP22-SQ NPs. : $p<0.01$; *: $p<0.001$, #: $p<0.05$; ###: $p<0.001$ (Anova followed by Bonferroni tests).
Figure 19:
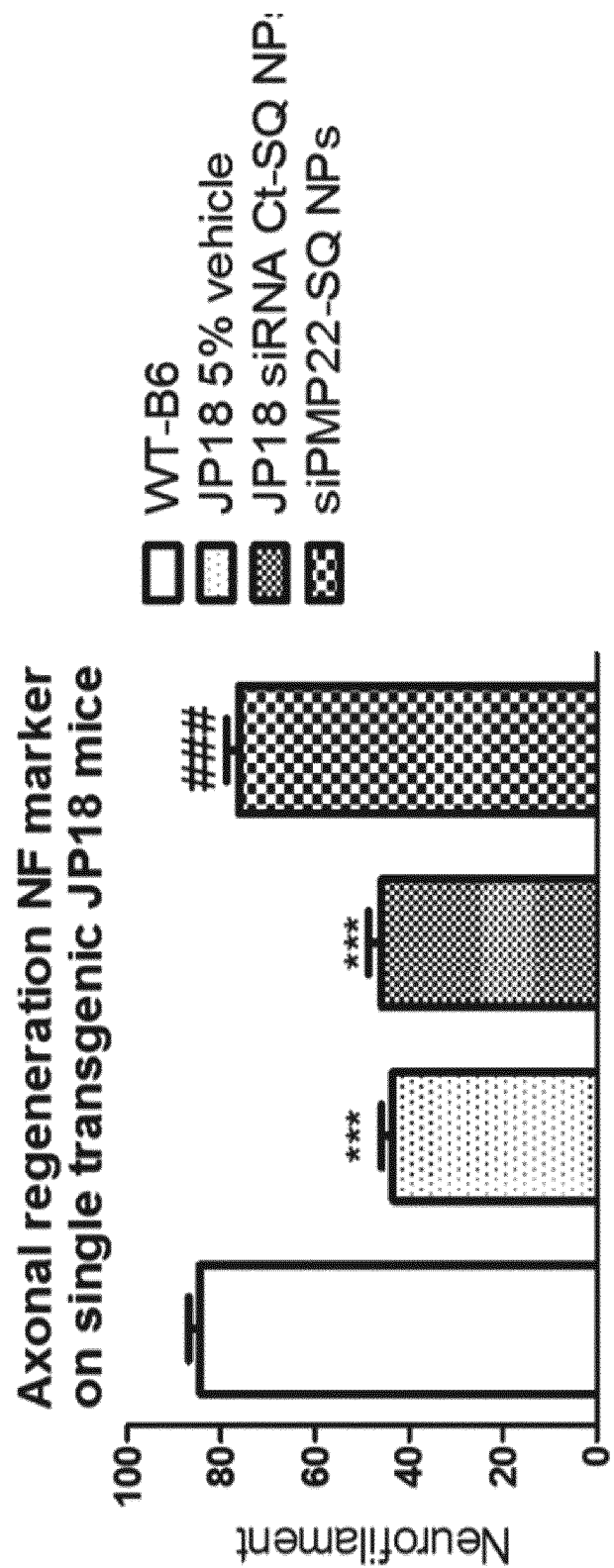
FIG. 19: Quantification analysis of the level of axonal regeneration NF marker on single transgenic JP18 mice. Data represents mean±SD and each group consists of three different mice. * represents the significance between WT-B6 group and the other groups and # represent significance between JP18 5% dextrose and JP18siPMP22-SQ NPs. ***: $p<0.001$, ###: $p<0.001$ (Anova followed by Bonferroni tests).
Figure 20:
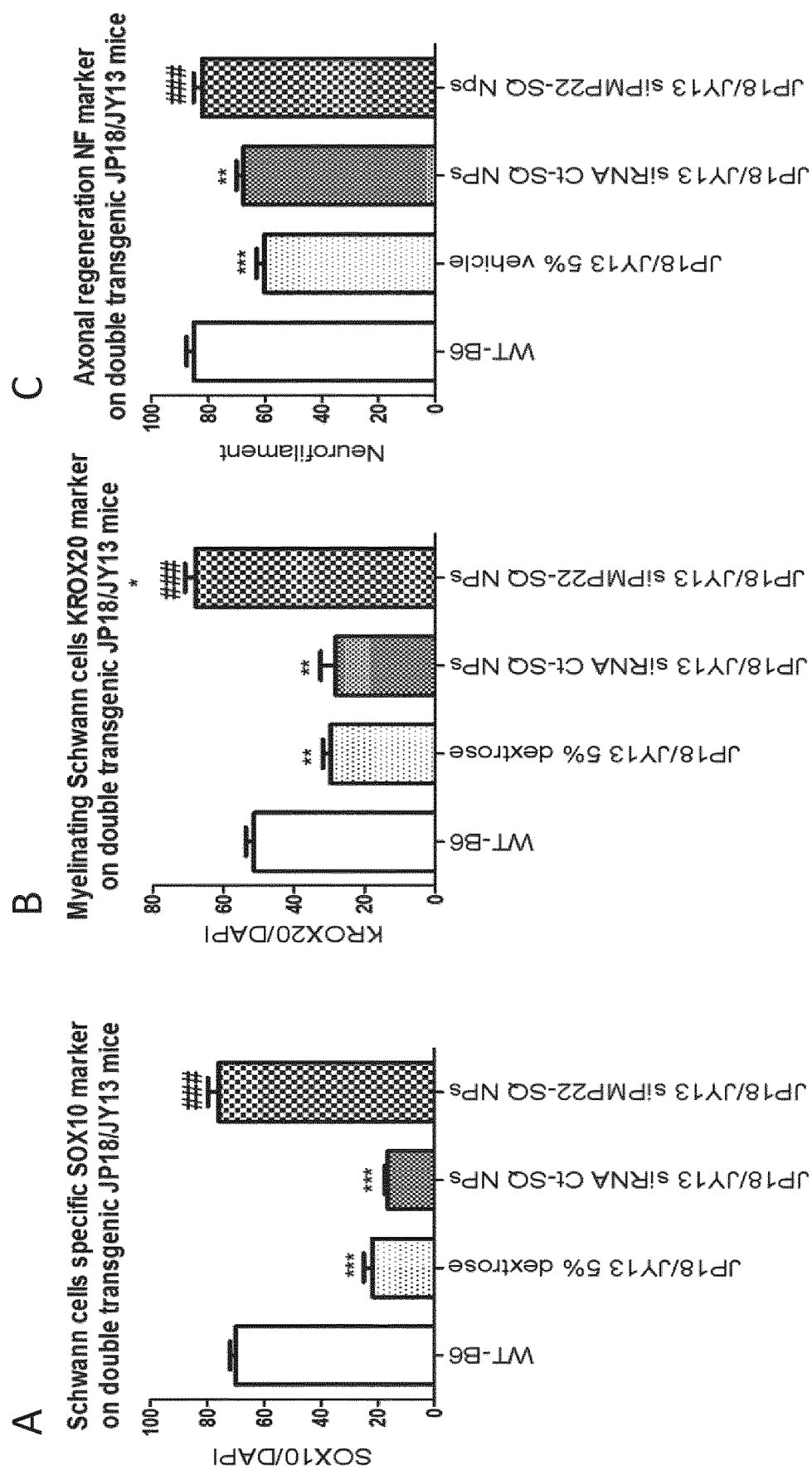
FIG. 20: Quantification analysis of Schwann cell markers SOX10 (A) and KROX20 (B) and axonal regeneration NF marker (C) on double transgenic JP18/JY13 CMT1A mice. Data show mean±SD and each group consists of three different mice. * represents the significance between WT-B6 group and the other groups and # represent significance between JP18/JY13 5% dextrose and JP18/JY13 siPMP22-SQ NPs. *: $p<0.05$; : $p<0.01$; *: $p<0.001$, ###: $p<0.001$ (Anova followed by Bonferroni tests).

Then the expression of proteins involved in myelination and axonal regeneration was analyzed in the simple transgenic mouse model. The levels of transcriptional factor SOX 10, myelination factor KROX20 and axonal regeneration NF marker were diminished in the JP18 5% dextrose and siRNA Ct groups; notably, siPMP22-SQ NPs treatment significantly increased their levels compared to the JP18 5% dextrose group (see FIGS. 18 A and B and 19). Similar results were obtained in the double transgenic mouse model: siPMP22-SQ NPs treatment increased myelination transcription factors (SOX10 and KROX20) and enhanced axonal regeneration compared to the JP18/JY13 5% dextrose group (see FIG. 20).

Long-Term Effect of the siRNA PMP22-SQ NPs on the Behavior of Double Transgenic Mice Long lasting effect of siPMP22-SQ NPs treatment on beam walking, locotronic and grip strength test was then analyzed. Double transgenic JP18/JY13 B6 mice received two cycles of treatment of 2.5 mg/Kg per cycle. Treatment was stopped for 21 days in between the two cycles to study the relapse. The mice were followed weekly to analyze the recovery and relapse periods.

Figure 21:
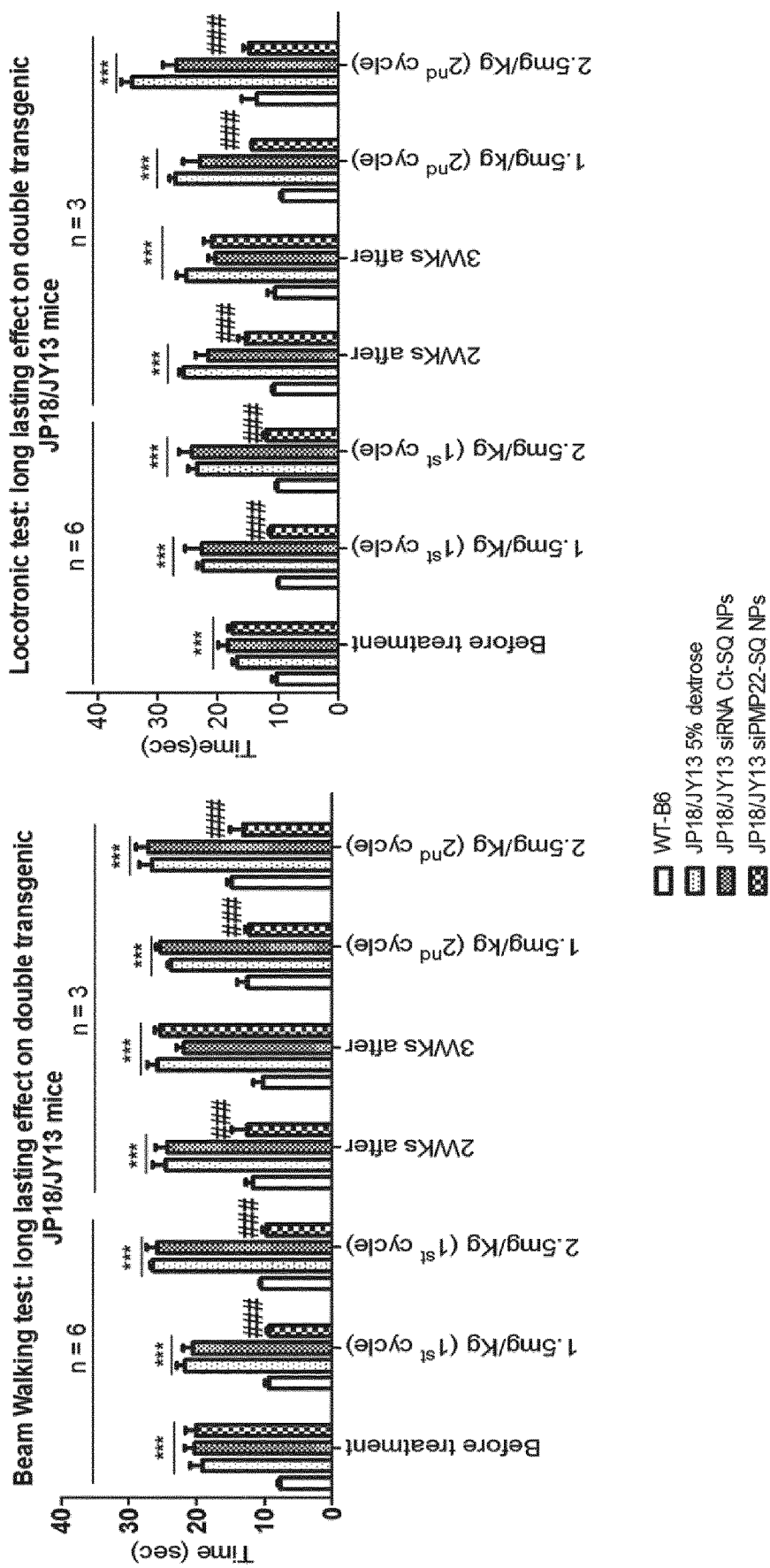
FIG. 21: Long lasting effect analysis of Beam walking and locotronic on double transgenic JP18/JY13 transgenic mice. JP18/JY13 B6 mice received two cycles of treatment of 2.5 mg/Kg per cycle. Treatment was stopped for 21 days in between the two cycles to study the relapse Data of Beam walking test (left panel) represent time spent to cross the bar (mean±SD). Data of Locotronic test (right panel) represent time recorded by the computerized program (mean±SD). Mice were followed weekly to analyze the recovery and relapse periods. (*) represents the significance between WT-B6 and other groups. (#) represent the significance between JP18/JY13 5% dextrose and JP18/JY13 siPMP22-SQ NPs. , $p<0.01$, *$p<0.001$ (Anova followed by Bonferroni tests).
Figure 22:
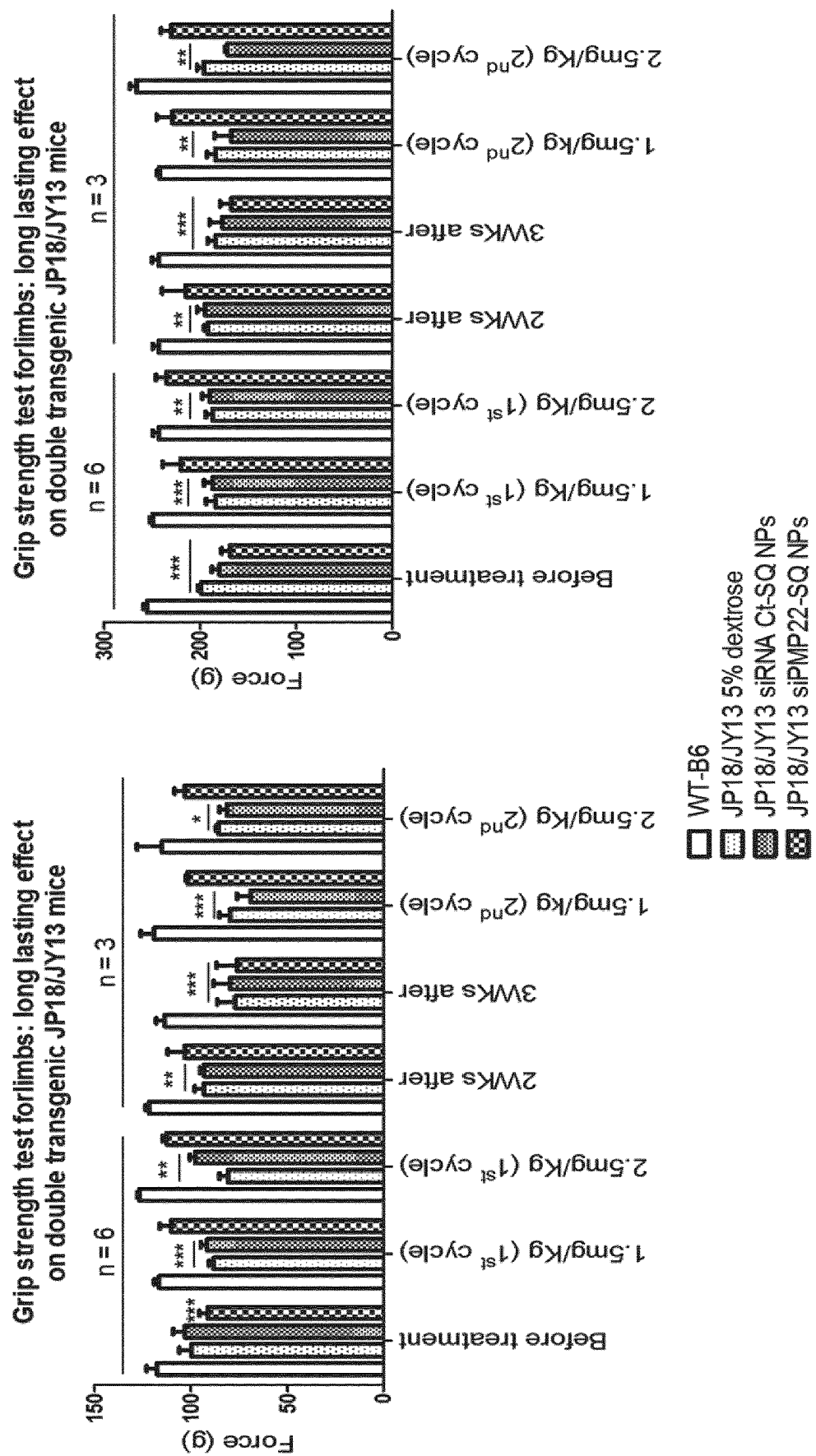
FIG. 22: Long lasting effect analysis of Grip strength test on double transgenic JP18/JY13 transgenic mice. JP18/JY13 B6 mice received two cycles of treatment of 2.5 mg/Kg per cycle. Treatment was stopped for 21 days in between the two cycles to study the relapse. Data of grip strength test (left panel) represent force exerted by the mice on the fore limbs (mean±SD). Data of grip strength test (right panel) force exerted by the mice on the total limbs (mean±SD). Mice were followed weekly to analyze the recovery and relapse periods. (*) represents the significance between WT-B6 and other groups. (#) represent the significance between JP18/JY13 5% dextrose and JP18/JY13 siPMP22-SQ NPs. , $p<0.01$, * $p<0.001$ (Anova followed by Bonferroni tests).

Motor activity of JP18/JY13 mice was restored from a dose of 1.5 mg/kg (11 days after the $1^{st}$ injection) and this effect lasted 15 days after the last treatment (approximately 30 days after the $1^{st}$ injection). However, there was a relapse 37 days after the $1^{st}$ injection. From the same dose in the second cycle of treatment (1.5 mg/kg, 11 days after the $1^{st}$ injection of the $2^{nd}$ cycle), mice walked as the wild-type mice. Remission was complete at the end the second cycle of treatment (see FIG. 21). The same result profile was observed for grip strength (see FIG. 22).

CONCLUSION

CMT-1A disease is the most common type of Charcot Marie Tooth (CMT) pathology and accounts for 40-50% of the cases of CMT. This original approach aims to develop a new therapy for CMT-1A disease by targeting the over expression of peripheral myelin protein 22 (PMP22), in particular by siRNA.

An siRNA against PMP22 able to counteract the 50% overexpression of PMP22 due to 1.5 Mb duplication on chromosome 17p11.2 was successfully developed, thus restoring the normal level of PMP22 expression. Importantly, the knockdown of PMP22 did not affect MPZ (P0) involved with PMP22 in the myelination process (dysregulation of MPZ may lead to CMT1B another type of CMT). Moreover, the mentioned siRNA did not affect the viability of cells.

Then, to protect and safely deliver the siRNA targeting PMP22, a "click chemistry squalenoylation approach" was developed. The bioconjugation of the siRNA PMP22 to squalene was quasi complete and gave a reaction yield of 95%. The siRNA PMP22-SQ NPs were still active after bio-conjugation with squalene, due to modification only in the passenger sense strand. After nanoprecipitation, the resulting nanoparticles were stable for 30 days with a size ~180 nm and a low polydispersity index of 0.14 displaying that these nanoparticles can be be injected intravenously.

Interestingly, it was demonstrated in transgenic mouse model of CMT-1A where the PMP22 was 1.5-fold overexpressed that these nanoparticles siRNA PMP22-SQ injected via intravenous route were able to restore the motor activity of CMT-1A mice which became identical to the wild type mice. This demonstration was done on two genetic backgrounds of mice B6 and CBA and gave similar results. Similar results were obtained using double transgenic JP18/JY13 B6 mice.

There is no equivalent study available neither in Europe nor in other parts of the world that describe a restoration of a motor activity in mice by knocking down of 50% the expression of a gene by siRNAs thanks to a regulation at fine-tuning of PMP22 expression in CMT-1A, which is the major form of CMT pathology.

The invention claimed is:

1. A method for treating Charcot-Marie-Tooth 1A (CMT-1A), wherein said method comprises administering to a subject in need thereof an antisense RNA targeting an mRNA encoding PMP22 protein, wherein said antisense RNA is a siRNA, wherein said antisense RNA has a length of from 12 to 50 nucleotides and wherein said antisense RNA is complementary to a portion consisting of or comprised within:
 nucleotides 989 to 1007 of sequence SEQ ID NO: 11,
 nucleotides 970 to 988 of sequence SEQ ID NO: 9,
 nucleotides 1721 to 1739 of sequence SEQ ID NO: 11,
 nucleotides 1726 to 1744 sequence SEQ ID NO: 9,
 nucleotides 431 to 449 of sequence SEQ ID NO: 11,
 nucleotides 429 to 447 sequence SEQ ID NO: 9,
 nucleotides 1805 to 1823 of sequence SEQ ID NO: 11,
 nucleotides 1809 to 1827 sequence SEQ ID NO: 9,
 nucleotides 921 to 939 of sequence SEQ ID NO: 11, or
 nucleotides 903 to 921 sequence SEQ ID NO: 9.

2. The method according to claim 1, wherein said antisense RNA reduces from 40% to 60% the amount of PMP22 protein in cells.

3. The method according to claim 1, wherein said antisense RNA comprises at least 10 consecutive nucleotides of a sequence selected from the group consisting of sequence SEQ ID NO: 15, SEQ ID NO: 16, SEQ ID NO: 17, SEQ ID NO: 18 and SEQ ID NO: 19.

4. The method according to claim 1, wherein said antisense RNA is an siRNA comprising one or two single-stranded overhang(s).

5. The method according to claim 1, wherein said antisense RNA is an siRNA comprising or consisting of (i) a sequence selected from the group consisting of sequence SEQ ID NO: 15, SEQ ID NO: 16, SEQ ID NO:17, SEQ ID NO: 18 and SEQ ID NO: 19 and (ii) optionally, one or two single-stranded overhang(s).

6. The method according to claim 1, wherein said antisense RNA is provided in the form of nanoparticles comprising said antisense RNA.

7. The method according to claim 1, wherein said antisense RNA is administered intravenously, intraperitoneally, subcutaneously or intranervously.

8. The method according to claim 1, wherein said antisense RNA is used in combination with at least another drug useful in the treatment of Charcot-Marie-Tooth 1A.

9. An antisense RNA targeting an mRNA encoding PMP22 protein, wherein said antisense RNA is a nucleic acid complementary to:
 (i) a portion consisting of or comprised within:
  nucleotides 970 to 988 of sequence SEQ ID NO: 9,
  nucleotides 431 to 449 of sequence SEQ ID NO: 11,
  nucleotides 429 to 447 sequence SEQ ID NO: 9, (ii) a portion consisting:
nucleotides 1721 to 1739 of sequence SEQ ID NO: 11,
nucleotides 1726 to 1744 sequence SEQ ID NO: 9,
nucleotides 1805 to 1823 of sequence SEQ ID NO: 11,
nucleotides 1809 to 1827 sequence SEQ ID NO: 9,
wherein said antisense RNA is a siRNA, and
said antisense RNA has a length of from 12 to 50 nucleotides.

10. The antisense RNA targeting PMP22 according to claim 9, wherein said antisense RNA is an siRNA comprising one or two single-stranded overhang(s).

11. The antisense RNA targeting PMP22 according to claim 9, wherein said antisense RNA is an siRNA comprising or consisting of (i) a sequence selected from the group consisting of sequence SEQ ID NO: 16, SEQ ID NO: 17 and SEQ ID NO: 18 and (ii) optionally, one or two single-stranded overhang(s).

12. A nanoparticle comprising the antisense RNA according to claim 9.

13. The nanoparticle according to claim 12, wherein the antisense RNA is coupled to squalene or a derivative thereof.

* * * * *

SEQUENCE LISTING

```
<160> NUMBER OF SEQ ID NOS: 19

<210> SEQ ID NO 1
<211> LENGTH: 19
<212> TYPE: RNA
<213> ORGANISM: Artificial Sequence
<220> FEATURE:
<223> OTHER INFORMATION: Synthetic siRNA targeting PMP22

<400> SEQUENCE: 1
ggcucuguuc cuguucuuc                                                 19

<210> SEQ ID NO 2
<211> LENGTH: 19
<212> TYPE: RNA
<213> ORGANISM: Artificial Sequence
<220> FEATURE:
<223> OTHER INFORMATION: Synthetic siRNA targeting PMP22

<400> SEQUENCE: 2
accuauuuau aacacuuuu                                                 19

<210> SEQ ID NO 3
<211> LENGTH: 19
<212> TYPE: RNA
<213> ORGANISM: Artificial Sequence
<220> FEATURE:
<223> OTHER INFORMATION: Synthetic siRNA targeting PMP22

<400> SEQUENCE: 3
acaauaaaua aaucucaaa                                                 19

<210> SEQ ID NO 4
<211> LENGTH: 19
<212> TYPE: RNA
```

```
<213> ORGANISM: Artificial Sequence
<220> FEATURE:
<223> OTHER INFORMATION: Synthetic siRNA targeting PMP22

<400> SEQUENCE: 4
ccucguguug aaucuuaaa                                                        19

<210> SEQ ID NO 5
<211> LENGTH: 19
<212> TYPE: RNA
<213> ORGANISM: Artificial Sequence
<220> FEATURE:
<223> OTHER INFORMATION: Synthetic siRNA targeting PMP22

<400> SEQUENCE: 5
ccaccaacug uagauguau                                                        19

<210> SEQ ID NO 6
<211> LENGTH: 19
<212> TYPE: RNA
<213> ORGANISM: Artificial Sequence
<220> FEATURE:
<223> OTHER INFORMATION: Synthetic siRNA targeting PMP22

<400> SEQUENCE: 6 cguccaggc caccaugau                                                         19

<210> SEQ ID NO 7
<211> LENGTH: 19
<212> TYPE: RNA
<213> ORGANISM: Artificial Sequence
<220> FEATURE:
<223> OTHER INFORMATION: Synthetic siRNA targeting PMP22

<400> SEQUENCE: 7
auaccaacug uguggacua                                                        19

<210> SEQ ID NO 8
<211> LENGTH: 19
<212> TYPE: RNA
<213> ORGANISM: Artificial Sequence
<220> FEATURE:
<223> OTHER INFORMATION: Synthetic siRNA targeting PMP22

<400> SEQUENCE: 8
aaaccuauuu auaacacuu                                                        19

<210> SEQ ID NO 9
<211> LENGTH: 1861
<212> TYPE: DNA
<213> ORGANISM: Homo sapiens
<220> FEATURE:
<221> NAME/KEY: CDS
<222> LOCATION: (239)..(721)

<400> SEQUENCE: 9
aataaactgg aaagacgcct ggtctggctt cagttacagg gagcaccacc agggaacatc           60
tcggggagcc tggttggaag ctgcaggctt agtctgtcgg ctgcgggtct ctgactgccc          120
tgtggggagg gtcttgcctt aacatcccct gcatttggct gcaaagaaat ctgcttggaa          180
gaaggggtta cgctgtttgg ccgggcagaa actccgctga gcagaacttg ccgccaga            238 atg ctc ctc ctg ttg ctg agt atc atc gtc ctc cac gtc gcg gtg ctg            286
Met Leu Leu Leu Leu Leu Ser Ile Ile Val Leu His Val Ala Val Leu
 1               5                  10                  15
```

| | | |
|---|---|---|
| gtg ctg ctg ttc gtc tcc acg atc gtc agc caa tgg atc gtg ggc aat<br>Val Leu Leu Phe Val Ser Thr Ile Val Ser Gln Trp Ile Val Gly Asn<br>20               25              30 | | 334 |
| gga cac gca act gat ctc tgg cag aac tgt agc acc tct tcc tca gga<br>Gly His Ala Thr Asp Leu Trp Gln Asn Cys Ser Thr Ser Ser Ser Gly<br>35              40              45 | | 382 |
| aat gtc cac cac tgt ttc tca tca tca cca aac gaa tgg ctg cag tct<br>Asn Val His His Cys Phe Ser Ser Ser Pro Asn Glu Trp Leu Gln Ser<br>50               55              60 | | 430 |
| gtc cag gcc acc atg atc ctg tcg atc atc ttc agc att ctg tct ctg<br>Val Gln Ala Thr Met Ile Leu Ser Ile Ile Phe Ser Ile Leu Ser Leu<br>65               70              75              80 | | 478 |
| ttc ctg ttc ttc tgc caa ctc ttc acc ctc acc aag ggg ggc agg ttt<br>Phe Leu Phe Phe Cys Gln Leu Phe Thr Leu Thr Lys Gly Gly Arg Phe<br>85               90              95 | | 526 |
| tac atc act gga atc ttc caa att ctt gct ggt ctg tgc gtg atg agt<br>Tyr Ile Thr Gly Ile Phe Gln Ile Leu Ala Gly Leu Cys Val Met Ser<br>100            105            110 | | 574 |
| gct gcg gcc atc tac acg gtg agg cac ccg gag tgg cat ctc aac tcg<br>Ala Ala Ala Ile Tyr Thr Val Arg His Pro Glu Trp His Leu Asn Ser<br>115            120            125 | | 622 |
| gat tac tcc tac ggt ttc gcc tac atc ctg gcc tgg gtg gcc ttc ccc<br>Asp Tyr Ser Tyr Gly Phe Ala Tyr Ile Leu Ala Trp Val Ala Phe Pro<br>130            135            140 | | 670 |
| ctg gcc ctt ctc agc ggt gtc atc tat gtg atc ttg cgg aaa cgc gaa<br>Leu Ala Leu Leu Ser Gly Val Ile Tyr Val Ile Leu Arg Lys Arg Glu<br>145            150            155            160 | | 718 |
| tga ggcgcccaga cggtctgtct gaggctctga gcgtacatag ggaagggagg | | 771 |
| aagggaaaac agaaagcaga caaagaaaaa agagctagcc caaaatccca aactcaaacc | | 831 |
| aaaccaaaca gaaagcagtg gaggtggggg ttgctgttga ttgaagatgt atataatatc | | 891 |
| tccggtttat aaaacctatt tataacactt tttacatata tgtacatagt attgtttgct | | 951 |
| ttttatgttg accatcagcc tcgtgttgag ccttaaagaa gtagctaagg aactttacat | | 1011 |
| cctaacagta taatccagct cagtattttt gttttgtttt ttgtttgttt gttttgtttt | | 1071 |
| acccagaaat aagataactc catctcgccc cttcccttc atctgaaaga agataccctcc | | 1131 |
| ctcccagtcc acctcattta gaaaaccaaa gtgtgggtag aaaccccaaa tgtccaaaag | | 1191 |
| ccctttctg gtgggtgacc cagtgcatcc aacagaaaca gccgctgccc gaacctctgt | | 1251 |
| gtgaagcttt acgcgcacac ggacaaaatg cccaaactgg agcccttgca aaaacacggc | | 1311 |
| ttgtggcatt ggcatacttg cccttacagg tggagtatct tcgtcacaca tctaaatgag | | 1371 |
| aaatcagtga caacaagtct ttgaaatggt gctatggatt taccattcct tattatcact | | 1431 |
| aatcatctaa acaactcact ggaaatccaa ttaacaattt tacaacataa gatagaatgg | | 1491 |
| agacctgaat aattctgtgt aatataaatg gtttataact gcttttgtac ctagctaggc | | 1551 |
| tgctattatt actataatga gtaaatcata aagccttcat cactcccaca tttttcttac | | 1611 |
| ggtcggagca tcagaacaag cgtctagact ccttgggacc gtgagttcct agagcttggc | | 1671 |
| tgggtctagg ctgttctgtg cctccaagga ctgtctggca atgacttgta ttggccacca | | 1731 |
| actgtagatg tatatatggt gcccttctga tgctaagact ccagacccttt tgttttgct | | 1791 |
| ttgcattttc tgattttata ccaactgtgt ggactaagat gcattaaaat aaacatcaga | | 1851 |
| gtaactcact | | 1861 |

<210> SEQ ID NO 10
<211> LENGTH: 160

```
<212> TYPE: PRT
<213> ORGANISM: Homo sapiens

<400> SEQUENCE: 10

Met Leu Leu Leu Leu Leu Ser Ile Ile Val Leu His Val Ala Val Leu
1               5                   10                  15

Val Leu Leu Phe Val Ser Thr Ile Val Ser Gln Trp Ile Val Gly Asn
            20                  25                  30

Gly His Ala Thr Asp Leu Trp Gln Asn Cys Ser Thr Ser Ser Ser Gly
        35                  40                  45

Asn Val His His Cys Phe Ser Ser Pro Asn Glu Trp Leu Gln Ser
    50                  55                  60

Val Gln Ala Thr Met Ile Leu Ser Ile Ile Phe Ser Ile Leu Ser Leu
65              70                  75                  80

Phe Leu Phe Phe Cys Gln Leu Phe Thr Leu Thr Lys Gly Gly Arg Phe
                85                  90                  95

Tyr Ile Thr Gly Ile Phe Gln Ile Leu Ala Gly Leu Cys Val Met Ser
            100                 105                 110

Ala Ala Ala Ile Tyr Thr Val Arg His Pro Glu Trp His Leu Asn Ser
        115                 120                 125

Asp Tyr Ser Tyr Gly Phe Ala Tyr Ile Leu Ala Trp Val Ala Phe Pro
    130                 135                 140

Leu Ala Leu Leu Ser Gly Val Ile Tyr Val Ile Leu Arg Lys Arg Glu
145                 150                 155                 160

<210> SEQ ID NO 11
<211> LENGTH: 1865
<212> TYPE: DNA
<213> ORGANISM: Mus musculus

<400> SEQUENCE: 11
acacccttct gcagcgacgc aaatagggcg tagttcccgt taaaggggaa caccgggagc        60
ctcccactgc cccttgctt tgcgcgcgcg ctgacccgca gcacagctgt ctttggggac      120
gccagcaacc cagtggacgc accggagttt gtgcctgagg ctaatctgct ctgagatagc      180
tgtccctttg aactgaaaca ggcaccgctc tctgatccc gagcccaact cccagccacc      240
atgctcctac tcttgttggg gatcctgttc ctgcacatcg cggtgctagt gttgctcttc      300
gtctccacca tcgtcagcca atggctcgtg ggcaatggac acacgactga tctctggcag      360
aactgtacca catccgcctt gggagccgtc aacactgct actcctcatc agtgagcgaa      420
tggctgcagt ctgtccaggc caccatgatc ctgtctgtca tcttcagcgt cctggctctg      480
ttcctgttct ctgccagct cttcactctc accaaaggcg gccggtttta catcactgga      540
ttcttccaaa tccttgctgg tctgtgcgtg atgagtgcag cggccatcta cacagtgagg      600
cacagtgagt ggcatgtcaa cactgactac tcctatggct cgcctacat cctggcctgg      660 gtggcctttc ccctagccct cctcagtggt atcatctatg tgatcctgcg gaaacgcgaa      720
tgaggcgccc gacgacgcac cgtccgtcta ggctctgagc gcgcataggg tccacaggga      780
gggaggaagg aaaccagaga acaaaaccaa ccaaccaaaa aagagctagc cccaaaccca      840
aacgcaagcc aaaccaaaca gaacgcagtt gagtggggat tgctgttgat tgaagatgta      900
tataatatct atggtttata aaacctattt ataacacttt ttacatatat gtacatagga      960 ttgtttttgct tttatgttg accgtcagcc tcgtgttgaa tcttaaacaa ctttacatcc     1020
taacactata accaagctca gtatctttgt tttgtttcgt ttttttttt aatctttttg     1080
```

-continued

| | |
|---|---|
| ttttgctcag acataaaaac tccacgtggc cccctttcat ctgaaagcag atacctccct | 1140 |
| cccactcaac ctcataggat aaccaaagtg tggggacaaa ccccagacag ttgaagacct | 1200 |
| ttacactatg ggtgacccag tgcatttagc aggagtatcc actgcccgaa tccatgtgtg | 1260 |
| aagccctaag cactcacaga cgaaaagccc tgaccggaac cctctgcaaa acagtaata | 1320 |
| gctggtggct cctgaacact tgaccctgta gacggagtac tggggccaca cgtttaaatg | 1380 |
| agaagtcaga gacaagcaat ctgtgaaatg gtgctataga tttaccattc cttgttatta | 1440 |
| ctaatcgttt aaaccactca ctggaaactc aattaacagt tttatgcgat acagcagaat | 1500 |
| ggagacccga tacaaacggt tcataactgc tttcatacct agctaggctg ttgttattac | 1560 |
| tacaataaat aaatctcaaa gccttcgtca gtcccacagt tttctcacgg tcggagcatc | 1620 |
| aggacgagca tctagaccct tgggactagc gagttccctg gctttctggg tctagagtgt | 1680 |
| tctgtgcctc caaggactgt ctggcgatga cttgtattgg ccaccaactg tagatgtata | 1740 |
| tacggtgtcc ttctgatgct aagactccag acctttcttg tttttgcttg ctttctctga | 1800 |
| ttttatacca actgtgtgga ctaagatgca tcaaaataaa catcagagta actcaaaaaa | 1860 |
| aaaaa | 1865 |

```
<210> SEQ ID NO 12
<211> LENGTH: 19
<212> TYPE: RNA
<213> ORGANISM: Artificial Sequence
<220> FEATURE:
<223> OTHER INFORMATION: Synthetic as siRNA targeting PMP22

<400> SEQUENCE: 12
```

| | |
|---|---|
| gaagaacagg aacagagcc | 19 |

```
<210> SEQ ID NO 13
<211> LENGTH: 19
<212> TYPE: RNA
<213> ORGANISM: Artificial Sequence
<220> FEATURE:
<223> OTHER INFORMATION: Synthetic as siRNA targeting PMP22

<400> SEQUENCE: 13
```

| | |
|---|---|
| aaaaguguua uaaauaggu | 19 |

```
<210> SEQ ID NO 14
<211> LENGTH: 19
<212> TYPE: RNA
<213> ORGANISM: Artificial Sequence
<220> FEATURE:
<223> OTHER INFORMATION: Synthetic as siRNA targeting PMP22

<400> SEQUENCE: 14
```

| | |
|---|---|
| uuugagauuu auuuauugu | 19 |

```
<210> SEQ ID NO 15
<211> LENGTH: 19
<212> TYPE: RNA
<213> ORGANISM: Artificial Sequence
<220> FEATURE:
<223> OTHER INFORMATION: Synthetic as siRNA targeting PMP22

<400> SEQUENCE: 15
```

| | |
|---|---|
| uuuaagauuc aacacgagg | 19 |

```
<210> SEQ ID NO 16
<211> LENGTH: 19
```

```
<212> TYPE: RNA
<213> ORGANISM: Artificial Sequence
<220> FEATURE:
<223> OTHER INFORMATION: Synthetic as siRNA targeting PMP22

<400> SEQUENCE: 16
auacaucuac aguuggugg                                              19

<210> SEQ ID NO 17
<211> LENGTH: 19
<212> TYPE: RNA
<213> ORGANISM: Artificial Sequence
<220> FEATURE:
<223> OTHER INFORMATION: Synthetic as siRNA targeting PMP22

<400> SEQUENCE: 17
aucauggugg ccuggacag                                              19

<210> SEQ ID NO 18
<211> LENGTH: 19
<212> TYPE: RNA
<213> ORGANISM: Artificial Sequence
<220> FEATURE:
<223> OTHER INFORMATION: Synthetic as siRNA targeting PMP22

<400> SEQUENCE: 18
uaguccacac aguugguau                                              19

<210> SEQ ID NO 19
<211> LENGTH: 19
<212> TYPE: RNA
<213> ORGANISM: Artificial Sequence
<220> FEATURE:
<223> OTHER INFORMATION: Synthetic as siRNA targeting PMP22

<400> SEQUENCE: 19
aaguguuaua aauagguuu                                              19
```